United States Patent
Frey et al.

(10) Patent No.: US 10,876,131 B2
(45) Date of Patent: Dec. 29, 2020

(54) DIG-303 INSECTICIDAL CRY TOXINS

(71) Applicant: DOW AGROSCIENCES LLC, Indianapolis, IN (US)

(72) Inventors: Meghan L. F. Frey, Greenwood, IN (US); Justin M. Lira, Zionsville, IN (US); Xiaoping Xu, Carmel, IN (US); Ignacio Mario Larrinua, Indianapolis, IN (US); Kenneth Narva, Zionsville, IN (US); Timothy D Hey, Zionsville, IN (US)

(73) Assignee: DOW AGROSCIENCES LLC, Indianpolis, IN (US)

(*) Notice: Subject to any disclaimer, the term of this patent is extended or adjusted under 35 U.S.C. 154(b) by 221 days.

(21) Appl. No.: 14/928,106

(22) Filed: Oct. 30, 2015

(65) Prior Publication Data

US 2016/0122399 A1    May 5, 2016

Related U.S. Application Data

(60) Provisional application No. 62/073,649, filed on Oct. 31, 2014.

(51) Int. Cl.
C12N 15/82    (2006.01)
C07K 14/325   (2006.01)

(52) U.S. Cl.
CPC ........ C12N 15/8286 (2013.01); C07K 14/325 (2013.01); *Y02A 40/162* (2018.01)

(58) Field of Classification Search
None
See application file for complete search history.

(56) References Cited

U.S. PATENT DOCUMENTS

| | | |
|---|---|---|
| 4,693,976 A | 9/1987 | Schilperoort et al. |
| 4,762,785 A | 8/1988 | Comai |
| 5,141,131 A | 8/1992 | Miller, Jr. et al. |
| 5,149,645 A | 9/1992 | Hoekema et al. |
| 5,159,135 A | 10/1992 | Umbeck |
| 5,177,010 A | 1/1993 | Goldman et al. |
| 5,231,019 A | 7/1993 | Paszkowski et al. |
| 5,380,831 A | 1/1995 | Adang et al. |
| 5,463,174 A | 10/1995 | Moloney et al. |
| 5,464,763 A | 11/1995 | Schilperoort et al. |
| 5,608,142 A | 3/1997 | Barton et al. |
| 5,679,558 A | 10/1997 | Gobel et al. |
| 5,736,131 A | 4/1998 | Bosch et al. |
| 6,037,526 A | 3/2000 | Grimsley et al. |
| 6,074,877 A | 6/2000 | D'Halluin et al. |
| 6,090,931 A | 7/2000 | Edwards et al. |
| 6,204,246 B1 | 3/2001 | Bosch et al. |
| 6,376,234 B1 | 4/2002 | Grimsley et al. |
| 6,780,408 B1 | 8/2004 | Bosch et al. |
| 7,060,876 B2 | 6/2006 | Hiei et al. |
| 7,230,167 B2 | 6/2007 | Chen et al. |
| 7,618,942 B2 | 11/2009 | Malvar et al. |
| 2010/0298207 A1* | 11/2010 | Sampson ............... A01N 63/02 514/2.4 |
| 2010/0319093 A1 | 12/2010 | Lira et al. |
| 2011/0203014 A1 | 8/2011 | Sampson et al. |
| 2012/0311746 A1 | 12/2012 | Meade et al. |
| 2014/0245491 A1 | 8/2014 | Sampson et al. |

FOREIGN PATENT DOCUMENTS

| | | |
|---|---|---|
| WO | WO 2008/121633 | 10/2008 |
| WO | WO 2010/099365 | 9/2010 |
| WO | WO 2010/120452 | 10/2010 |
| WO | WO 2013/022743 | 2/2013 |

OTHER PUBLICATIONS

Guo et al., Proc. Natl. Acad. Sci. USA 101:9205-10 (2004).*
De Maagd et al., Trends Genet. 17:193-99 (2001).*
Aronson et al., FEMS Microbiol. Lett. 195:1-8 (2001).*
De Maagd et al., Appl. Environ Microbiol 65:4369-4374 (1999).*
Tounsi et al., J. Appl. Microbiol. 95:23-28 (2003).*
Angsuthanasombat et al., J Biochem Mol Biol 34:402-407 (2001).*
Argolo-Filho & Loguercio, Insects 5:62-91 (2014).*
Aronson, A. I., Geng, C., Wu. L. (1999) Aggregation of Bacillus thuringiensis Cry1A toxins upon binding to target insect larval midgut vesicles. Appl. Environ. Microbiol. 65:2503-2507.
Bravo, A., Gill, S. S., Soberon, M. (2007) Mode of action of Bacillus thuringiensis Cry and Cyt toxins and their potential for insect control. Toxicon 49:423-435.
Crickmore N., Zeigler, D.R., Feitelson J., Schnepf, E., Van Rie J., Lereclus D., Baum J., and Dean D.H. (1998) Revision of the Nomenclature for the Bacillus thuringiensis Pesticidal Crystal Proteins Microbiol. Mol. Biol. Reviews 62:807-813.
De Maagd, R. A., Bravo, A., Berry, C., Crickmore, N., Schnepf, E. (2003) Structure, diversity, and evolution of protein toxins from spore-forming entomopathogenic bacteria. Annu. Rev. Genet. 37:409-433.
Koiwa, H., Shade, R. E., Zhu-Salzman, K., D'Urzo, M. P., Murdock, L. L., Bressan, R. A., Hasegawa, P. M. (2000) A plant defensive cystatin (soyacystatin) targets cathepsin L-like digestive cysteine proteinases (DvCALs) in the larval midgut of western corn rootworm *Diabrotica virgifera* virgifera. FEBS Letters 471:67-70.
Narva et al. "Transgenic approached to Western Corn Rootworm Control," Adv. Biochem. Eng. Biotechnol. (2013) 136: 135-162.
Geneseq Database accession No. BBM50037, "Bacillus thuringiensis Axmi231 protein, SEQ ID 29," (Oct. 23, 2014), EBI—XP002777983.
Naimov et al., "A hybrid *Bacillus thuringiensis* delta-endotoxin gives resistance against a coleopteran and a lepidopteran pest in transgenic potato," Plant Biotechnology Journal, 1(1): 51-57 (Jan. 1, 2003).
Angsuthanasombat et al., J Biochem Mol Bioi 34:402-407 (2001).
Tounsi et al., J. Apl. Microbiol. 95:23-28 (2003).
Balasubramanian P, Jayakumar R, Shambharkar P, Unnamalai N, Pandian SK, Kumaraswami NS, Ilangovan R, Sekar V. (2002) Cloning and characterization of the crystal protein-encoding gene of Bacillus thuringiensis subsp. yunnanensis. Appl. Environ. Micorbiol. 68:408-411.

(Continued)

Primary Examiner — Russell T Boggs

(57) ABSTRACT

DIG-303 insecticidal toxins, polynucleotides encoding such toxins, use of such toxins to control pests, and transgenic plants that produce such toxins are disclosed.

17 Claims, No Drawings

Specification includes a Sequence Listing.

(56) References Cited

OTHER PUBLICATIONS

Chambers J A, Jelen A, Gilbert M P, Jany C S, Johnson T B, Gawron-Burke C. (1991) Isolation and characterization of a novel insecticidal crystal protein gene from Bacillus lhuringiensis subsp. aizawai. J Bacteriology. 173(13): 3966-76.

Donovan WP, Rupar M J, Slaney AC, Malvar T, Gawron-Burke MC, Johnson TB. (1992) Characterization of two genes encoding Bacillus thuringiensis insecticidal crystal proteins toxic to Coleoptera species. Appl. Environ. Microbiol. 58 (12): 3921-7.

GenBank Accession No. BAB78602 (2001).

GenBank Accession No. BAB78603 (2001).

GenBank Accession No. BAB78604 (2001).

International Search Report and Written Opinion for International Application No. PCT/US15/58371, dated Feb. 10, 2016.

* cited by examiner

SEQUENCE LISTING

<160> NUMBER OF SEQ ID NOS: 4

<210> SEQ ID NO 1
<211> LENGTH: 3771
<212> TYPE: DNA
<213> ORGANISM: Bacillus thuringiensis

<400> SEQUENCE: 1

```
atgaaccaaa attacaatca taatgaattt gaaatcatgg atactagtaa tatgggctat     60
cagccaaggt atccatttgc gaaggcacca agatcagaat tacaaaacat ggattataaa    120
gattggatga atagatgtac aagtgaagaa tcatttagcc aaggtacctc aaattctatt    180
agagatgccg ttattgcagg atcaaagatt gcaggaacaa tcatcggtgc agtttttcca    240
cctttaaaaa taccagcact gatcctaagt aatttgatcc catttttatg gccaaaggag    300
gctggacctc ctgggactcc tgaagcgcaa tttacatggg agcaaatgat gaatgctgtg    360
gaagaaatgg ttgatcaaaa aattgatact ttagtaaaag accaagcgat atcaacttta    420
caaatcttac agtcttatat tcaggattat caacaagcat tatgcaattt acaaactgat    480
cccaataatg agaaatataa agaggacgta agaagggaat ttaatgatgc cgaagatcag    540
gcgaaagccg ctatcatcca atttcggaat gtgaaatatg ccggtttatt actagccgat    600
tatgcacaag cagctaattt rcacctactt ttattacgag atgtcgtaca attcggagaa    660
agttggggat tttcggccct tgaagtgcaa caatattact cgaatgagag cctagtagga    720
aatcccggca tgaaacaact attagcaacc tatacggatc attgtgtacg ttggtataat    780
gagggattac aaaatagata tgaaacgggc aactggaata cattcaatga tttccgaaga    840
aatatgactc taatgatact agatatcgtg gcgatatggc caacttatga tccaatactc    900
tataccgttc ctactaaatc ccaacttaca cgaactgtgt atacaccttt tatacaaggt    960
tctctgagca tcaaaccact tacgatctca gttatagaaa ataatgtacc tgctcctcca   1020
gacctattta gatggttgcg tgagatagca ttttatgcgg aaggtcctgt cgcaccgggt   1080
agtagggtgc ttagtggtca gatacaacgc tatcagtata ctctgcgtga cctcttgtac   1140
gaggaggcta agggggagct tgtagaacaa gtgggaaccc ttgtggttcc acacccaaca   1200
tccgaagatg atgtttggtc gcttctgatg aattatagta aaattaatta cgtgccgtat   1260
cctatcatgg ctggcttgaa ctatttagac tttcatttaa ccaaaactgt ggatcagcga   1320
ataacttttc tcccagacca tgttagtaga aacgaaacat tcggactccc ttgtggtcct   1380
aatcctgcaa atgattgtga tccttgtgca ccttgtactg tacttcctaa cgtgagcgat   1440
ccttgtaatg acagatcact ttatagtcat cgattttcat atatgggtac gtatcctgct   1500
cagtatactt atcctggagg tcaggagtct gataatgaga gtgtttgcta cggctggaca   1560
catgtaagcg cagatgcaaa caatctgata gatgctgaaa ggattaccca aattccagcg   1620
gtgaaggcat accaaacaaa tggaaaagta atcaaaggtc ctggtagcac aggaggagat   1680
gtagtacagt tagtttcaga cacaggacaa gaccttcaga agctaaggat taggatgaaa   1740
gggcaagccc aaaaaggata tcaattacga attcgctatg caagttccgt gttttaccaa   1800
tctctaactg cagacaggta cgtaaatatt gatggttctt ggacgactgc cggggggagt   1860
aactttcagc tacggccaac atattcgggt gaatcgctaa actacaactc ttttggttat   1920
gctacgctgt ttacgtcgtt atatcctact ccttatgagg attgggagat agtattaaca   1980
tctaatagta ttcctcctat tatcatcgac aaaatcgaat tcattccaat cgaaggatcc   2040
gtggaagaat ttgaagcgaa tcaagcttta gaaaaggcaa gaaaggccgt gaataccttg   2100
```

```
tttacaggcg atgcgaaaaa tgctctaaaa ttgaacatca cagattacgc ggtagatcaa    2160
gctgctaatt tggcggagtg tgtatcagag gaattccatg cccaagaaaa aatgatccta    2220
ctggatcaag tgaaattcgc gaaacggctg agtcacgcac ggaatctatt aaaccatgga    2280
gattttgaat cgtcagattg gtctggtgaa atggatggaa aaacaagtcc tcatgtccat    2340
gtggcggcgg atcatccgat ctttaaagga cgatatctcc acatgccagg tgcgacaagc    2400
tcaccatttt ctagtcatgt atatccaact tatatctatc aaaaggtaga tgaatcgaaa    2460
ttaaaatcgt atacgygtta cctcgtacgt gggtttgtag gaaatagtaa ggacctagaa    2520
ttactggttg aacgatacgg aaaagatgtc catgtagaac tggatgtgcc aaatgacatc    2580
cagtattcct taccgatgaa tgaatgcggt ggatttgatc gatgccgacc tgtattctat    2640
caagctcgct cctctcatgc atgtacatgt aaggataccg cttccatgca tacgattgt     2700 cagtgtaaag acaaagtgaa tcgcacttcg gccgacgggt atacaaatgt actgacaggt    2760
agtatggtat atacgaatga attccatgcc cacaaatcct gtggctgcaa gaacaatgac    2820
atgtaccaga gcggaacaca tccgcataag tcttgtggat gcaaagaccc acatgtcttc    2880
acgtaccata ttgacacagg atgtgtggat caagaagaaa acgtaggtct attctttgct    2940
ttaaaaattg cgagcgaaaa tggtgttgcg aacatcgaca atctggaaat cattgaggca    3000
caaccactca caggtgaagc gttagcccgc gtgaaaaaac gcgaacagaa atggaaacaa    3060
gaaatggaac aaaaacgttt acaaacagag aaagccgtac aagcagcgca aggtrcgatt    3120
cagcccctmt tcacaaacgs gcagtacaat cgtttrmaat ttgaaacgyt gttcycgcaa    3180
attgtccgtg cagagwrgct cgtmcaacag atyccatatg tryaycaycc attcttgagt    3240
ggggcactgc tagccgtacc aggtatgaat tttgatattg tacaacaact ctctgccttg    3300
gttgatagag cacgaggatt atatgaccta cgaaatctcg tacaaaacgg tacattcagt    3360
agcggcacag gaaattggca tgtatcagaa ggcgtaaagg tgcagccact gcaaaataca    3420
tccgttcttg tcctatcgga atggaatcat gaagcgtctc agcaattacg tatcgatcca    3480
gatcgcggat atgtgttacg tgtaacagcc cgaaaagagg gkgctggaaa aggtacggtr    3540
acgatgagtg attgtgcaga ytatacagar acactgacct ttacatcwtg tgactayaay    3600
acgrtyggtw cccaarcgat gacaggtggt acgttatcgg gatttgtgac aaaaacgctg    3660
gaaatcttcc cagacacaga tcgcatccgt attgacatcg gtgaaacaga aggtacgttt    3720
aagattgaaa gtgtggaact gatttgtatg gaacagatgg agaacaacgg a             3771
```

<210> SEQ ID NO 2
<211> LENGTH: 1257
<212> TYPE: PRT
<213> ORGANISM: Bacillus thuringiensis
<220> FEATURE:
<221> NAME/KEY: misc_feature
<222> LOCATION: (826)..(826)
<223> OTHER INFORMATION: Xaa can be Cys or Arg, preferred Arg
<220> FEATURE:
<221> NAME/KEY: misc_feature
<222> LOCATION: (1039)..(1039)
<223> OTHER INFORMATION: Xaa can be Thr or Ala, preferred Ala
<220> FEATURE:
<221> NAME/KEY: misc_feature
<222> LOCATION: (1047)..(1047)
<223> OTHER INFORMATION: Xaa can be Gly or Ala, preferred Ala
<220> FEATURE:
<221> NAME/KEY: misc_feature
<222> LOCATION: (1053)..(1053)
<223> OTHER INFORMATION: Xaa can be Lys or Gln, preferred Gln
<220> FEATURE:

```
<221> NAME/KEY: misc_feature
<222> LOCATION: (1059)..(1059)
<223> OTHER INFORMATION: Xaa can be Pro or Ser, preferred Pro
<220> FEATURE:
<221> NAME/KEY: misc_feature
<222> LOCATION: (1066)..(1066)
<223> OTHER INFORMATION: Xaa can be Lys, Arg, or Trp, preferred Lys
<220> FEATURE:
<221> NAME/KEY: misc_feature
<222> LOCATION: (1075)..(1075)
<223> OTHER INFORMATION: Xaa can be His or Tyr, preferred Tyr
<220> FEATURE:
<221> NAME/KEY: misc_feature
<222> LOCATION: (1202)..(1202)
<223> OTHER INFORMATION: Xaa can be Ile or Val, preferred Val
<220> FEATURE:
<221> NAME/KEY: misc_feature
<222> LOCATION: (1204)..(1204)
<223> OTHER INFORMATION: Xaa can be Thr or Ser, preferred Ser
<220> FEATURE:
<221> NAME/KEY: misc_feature
<222> LOCATION: (1206)..(1206)
<223> OTHER INFORMATION: Xaa can be Thr or Ala, preferred Ala

<400> SEQUENCE: 2

Met Asn Gln Asn Tyr Asn His Asn Glu Phe Glu Ile Met Asp Thr Ser
 1               5                  10                  15

Asn Met Gly Tyr Gln Pro Arg Tyr Pro Phe Ala Lys Ala Pro Arg Ser
             20                  25                  30

Glu Leu Gln Asn Met Asp Tyr Lys Asp Trp Met Asn Arg Cys Thr Ser
         35                  40                  45

Glu Glu Ser Phe Ser Gln Gly Thr Ser Asn Ser Ile Arg Asp Ala Val
     50                  55                  60

Ile Ala Gly Ser Lys Ile Ala Gly Thr Ile Ile Gly Ala Val Phe Pro
 65                  70                  75                  80

Pro Leu Lys Ile Pro Ala Leu Ile Leu Ser Asn Leu Ile Pro Phe Leu
                 85                  90                  95

Trp Pro Lys Glu Ala Gly Pro Pro Gly Thr Pro Glu Ala Gln Phe Thr
            100                 105                 110

Trp Glu Gln Met Met Asn Ala Val Glu Glu Met Val Asp Gln Lys Ile
        115                 120                 125

Asp Thr Leu Val Lys Asp Gln Ala Ile Ser Thr Leu Gln Ile Leu Gln
    130                 135                 140

Ser Tyr Ile Gln Asp Tyr Gln Gln Ala Leu Cys Asn Leu Gln Thr Asp
145                 150                 155                 160

Pro Asn Asn Glu Lys Tyr Lys Glu Asp Val Arg Arg Glu Phe Asn Asp
                165                 170                 175

Ala Glu Asp Gln Ala Lys Ala Ala Ile Ile Gln Phe Arg Asn Val Lys
            180                 185                 190

Tyr Ala Gly Leu Leu Ala Asp Tyr Ala Gln Ala Ala Asn Leu His Leu
        195                 200                 205

Leu Leu Leu Arg Asp Val Val Gln Phe Gly Glu Ser Trp Gly Phe
    210                 215                 220

Ser Ala Leu Glu Val Gln Gln Tyr Tyr Ser Asn Glu Ser Leu Val Gly
225                 230                 235                 240

Asn Pro Gly Met Lys Gln Leu Leu Ala Thr Tyr Thr Asp His Cys Val
                245                 250                 255

Arg Trp Tyr Asn Glu Gly Leu Gln Asn Arg Tyr Glu Thr Gly Asn Trp
            260                 265                 270

Asn Thr Phe Asn Asp Phe Arg Arg Asn Met Thr Leu Met Ile Leu Asp
        275                 280                 285
```

```
Ile Val Ala Ile Trp Pro Thr Tyr Asp Pro Ile Leu Tyr Thr Val Pro
    290                 295                 300

Thr Lys Ser Gln Leu Thr Arg Thr Val Tyr Thr Pro Phe Ile Gln Gly
305                 310                 315                 320

Ser Leu Ser Ile Lys Pro Leu Thr Ile Ser Val Ile Glu Asn Asn Val
            325                 330                 335

Pro Ala Pro Pro Asp Leu Phe Arg Trp Leu Arg Glu Ile Ala Phe Tyr
            340                 345                 350

Ala Glu Gly Pro Val Ala Pro Gly Ser Arg Val Leu Ser Gly Gln Ile
        355                 360                 365

Gln Arg Tyr Gln Tyr Thr Leu Arg Asp Leu Leu Tyr Glu Glu Ala Lys
    370                 375                 380

Gly Glu Leu Val Glu Gln Val Gly Thr Leu Val Val Pro His Pro Thr
385                 390                 395                 400

Ser Glu Asp Asp Val Trp Ser Leu Leu Met Asn Tyr Ser Lys Ile Asn
            405                 410                 415

Tyr Val Pro Tyr Pro Ile Met Ala Gly Leu Asn Tyr Leu Asp Phe His
            420                 425                 430

Leu Thr Lys Thr Val Asp Gln Arg Ile Thr Phe Leu Pro Asp His Val
        435                 440                 445

Ser Arg Asn Glu Thr Phe Gly Leu Pro Cys Gly Pro Asn Pro Ala Asn
450                 455                 460

Asp Cys Asp Pro Cys Ala Pro Cys Thr Val Leu Pro Asn Val Ser Asp
465                 470                 475                 480

Pro Cys Asn Asp Arg Ser Leu Tyr Ser His Arg Phe Ser Tyr Met Gly
            485                 490                 495

Thr Tyr Pro Ala Gln Tyr Thr Tyr Pro Gly Gly Gln Glu Ser Asp Asn
        500                 505                 510

Glu Ser Val Cys Tyr Gly Trp Thr His Val Ser Ala Asp Ala Asn Asn
    515                 520                 525

Leu Ile Asp Ala Glu Arg Ile Thr Gln Ile Pro Ala Val Lys Ala Tyr
530                 535                 540

Gln Thr Asn Gly Lys Val Ile Lys Gly Pro Gly Ser Thr Gly Gly Asp
545                 550                 555                 560

Val Val Gln Leu Val Ser Asp Thr Gly Gln Asp Leu Gln Lys Leu Arg
            565                 570                 575

Ile Arg Met Lys Gly Gln Ala Gln Lys Gly Tyr Gln Leu Arg Ile Arg
            580                 585                 590

Tyr Ala Ser Ser Val Phe Tyr Gln Ser Leu Thr Ala Asp Arg Tyr Val
        595                 600                 605

Asn Ile Asp Gly Ser Trp Thr Thr Ala Gly Gly Ser Asn Phe Gln Leu
    610                 615                 620

Arg Pro Thr Tyr Ser Gly Glu Ser Leu Asn Tyr Asn Ser Phe Gly Tyr
625                 630                 635                 640

Ala Thr Leu Phe Thr Ser Leu Tyr Pro Thr Pro Tyr Glu Asp Trp Glu
            645                 650                 655

Ile Val Leu Thr Ser Asn Ser Ile Pro Pro Ile Ile Asp Lys Ile
            660                 665                 670

Glu Phe Ile Pro Ile Glu Gly Ser Val Glu Glu Phe Glu Ala Asn Gln
        675                 680                 685

Ala Leu Glu Lys Ala Arg Lys Ala Val Asn Thr Leu Phe Thr Gly Asp
    690                 695                 700
```

Ala Lys Asn Ala Leu Lys Leu Asn Ile Thr Asp Tyr Ala Val Asp Gln
705                 710                 715                 720

Ala Ala Asn Leu Ala Glu Cys Val Ser Glu Glu Phe His Ala Gln Glu
            725                 730                 735

Lys Met Ile Leu Leu Asp Gln Val Lys Phe Ala Lys Arg Leu Ser His
        740                 745                 750

Ala Arg Asn Leu Leu Asn His Gly Asp Phe Glu Ser Ser Asp Trp Ser
    755                 760                 765

Gly Glu Asn Gly Trp Lys Thr Ser Pro His Val His Val Ala Ala Asp
770                 775                 780

His Pro Ile Phe Lys Gly Arg Tyr Leu His Met Pro Gly Ala Thr Ser
785                 790                 795                 800

Ser Pro Phe Ser Ser His Val Tyr Pro Thr Tyr Ile Tyr Gln Lys Val
                805                 810                 815

Asp Glu Ser Lys Leu Lys Ser Tyr Thr Xaa Tyr Leu Val Arg Gly Phe
            820                 825                 830

Val Gly Asn Ser Lys Asp Leu Glu Leu Val Glu Arg Tyr Gly Lys
        835                 840                 845

Asp Val His Val Glu Leu Asp Val Pro Asn Asp Ile Gln Tyr Ser Leu
850                 855                 860

Pro Met Asn Glu Cys Gly Gly Phe Asp Arg Cys Arg Pro Val Phe Tyr
865                 870                 875                 880

Gln Ala Arg Ser Ser His Ala Cys Thr Cys Lys Asp Thr Ala Ser Met
                885                 890                 895

His Thr Asp Cys Gln Cys Lys Asp Lys Val Asn Arg Thr Ser Ala Asp
            900                 905                 910

Gly Tyr Thr Asn Val Leu Thr Gly Ser Met Val Tyr Thr Asn Glu Phe
        915                 920                 925

His Ala His Lys Ser Cys Gly Cys Lys Asn Asn Asp Met Tyr Gln Ser
930                 935                 940

Gly Thr His Pro His Lys Ser Cys Gly Cys Lys Asp Pro His Val Phe
945                 950                 955                 960

Thr Tyr His Ile Asp Thr Gly Cys Val Asp Gln Glu Glu Asn Val Gly
                965                 970                 975

Leu Phe Phe Ala Leu Lys Ile Ala Ser Glu Asn Gly Val Ala Asn Ile
            980                 985                 990

Asp Asn Leu Glu Ile Ile Glu Ala Gln Pro Leu Thr Gly Glu Ala Leu
        995                 1000                1005

Ala Arg Val Lys Lys Arg Glu Gln Lys Trp Lys Gln Glu Met Glu
1010                1015                1020

Gln Lys Arg Leu Gln Thr Glu Lys Ala Val Gln Ala Ala Gln Gly
1025                1030                1035

Xaa Ile Gln Pro Leu Phe Thr Asn Xaa Gln Tyr Asn Arg Leu Xaa
1040                1045                1050

Phe Glu Thr Leu Phe Xaa Gln Ile Val Arg Ala Glu Xaa Leu Val
1055                1060                1065

Gln Gln Ile Pro Tyr Val Xaa His Pro Phe Leu Ser Gly Ala Leu
1070                1075                1080

Leu Ala Val Pro Gly Met Asn Phe Asp Ile Val Gln Gln Leu Ser
1085                1090                1095

Ala Leu Val Asp Arg Ala Arg Gly Leu Tyr Asp Leu Arg Asn Leu
1100                1105                1110

Val Gln Asn Gly Thr Phe Ser Ser Gly Thr Gly Asn Trp His Val

```
        1115                1120                1125
Ser Glu Gly Val Lys Val Gln Pro Leu Gln Asn Thr Ser Val Leu
    1130                1135                1140

Val Leu Ser Glu Trp Asn His Glu Ala Ser Gln Gln Leu Arg Ile
    1145                1150                1155

Asp Pro Asp Arg Gly Tyr Val Leu Arg Val Thr Ala Arg Lys Glu
    1160                1165                1170

Gly Ala Gly Lys Gly Thr Val Thr Met Ser Asp Cys Ala Asp Tyr
    1175                1180                1185

Thr Glu Thr Leu Thr Phe Thr Ser Cys Asp Tyr Asn Thr Xaa Gly
    1190                1195                1200

Xaa Gln Xaa Met Thr Gly Gly Thr Leu Ser Gly Phe Val Thr Lys
    1205                1210                1215

Thr Leu Glu Ile Phe Pro Asp Thr Asp Arg Ile Arg Ile Asp Ile
    1220                1225                1230

Gly Glu Thr Glu Gly Thr Phe Lys Ile Glu Ser Val Glu Leu Ile
    1235                1240                1245

Cys Met Glu Gln Met Glu Asn Asn Gly
    1250                1255

<210> SEQ ID NO 3
<211> LENGTH: 3735
<212> TYPE: DNA
<213> ORGANISM: Artificial Sequence
<220> FEATURE:
<223> OTHER INFORMATION: Maize optimized

<400> SEQUENCE: 3
atggatacga gtaacatggg ctatcagcca cgctatccct tcgccaaagc tccaaggtcg     60
gaactccaga acatggacta caaagactgg atgaataggt gtaccagtga ggagtccttt    120
tcccaaggca cgtcgaactc cattcgggac gctgtcattg ctggctcaaa gattgctgga    180
accatcatag gtgccgtgtt tcctcccttg aagatcccag cgctgatact ctcgaatctc    240
atacccttct tgtggcctaa ggaagctggt cctcctggca cacccgaggc acagttcacc    300
tgggagcaga tgatgaacgc tgtggaagaa atggttgatc agaagattga cactctagtg    360
aaggatcaag caatcagtac tctccagatt ctccagtctt acatccaaga ctatcagcaa    420
gccctatgca acctacagac cgatcctaac aacgaaaagt acaaagagga tgttagacgg    480
gagttcaacg acgctgagga ccaagccaag gcagctatca tccagtttag aatgtgaag    540 tacgctggac tgttgctggc agactatgcc caagcagcca acttacacct cctgctactt    600
agggatgtgg ttcagttcgg agaatcgtgg ggtttctctg ctctggaggt tcagcagtac    660
tactccaacg aatctttagt tggaaaccct ggcatgaagc agctgttggc gacttacaca    720
gatcattgcg tgcgttggta caacgaaggc ttacagaatc gttacgagac tgggaattgg    780 aacacccttca cgactttag acgcaacatg acacttatga tccttgacat cgtagccatt    840
tggcctacgt atgaccccat actctacacc gtccctacga aatctcagct gacaaggacc    900
gtatacactc cgttcataca aggttcccct tccatcaaac cactgaccat tagcgtcatt    960
gagaacaacg tgcctgctcc acccgatctc ttccggtggc tgagggagat agccttctac   1020
gcagagggac ccgtagctcc tggctcaaga gtgctcagtg ccagatccga cgctatcag   1080 tacccctttc gcgatctctt gtacgaagaa gccaaaggcg agcttgtaga caagtcggc   1140 acactggtcg tgccacatcc gacgagtgag gatgacgtct ggtccctgct tatgaactac   1200
```

-continued

```
agtaagatca actacgtgcc atatcctatc atggctggac ttaactatct cgacttccac    1260
ctcacaaaga cagtggatca gaggatcacc ttcctgccag accacgtgag ccgtaacgag    1320
acctttgggc tgccatgcgg accaaatcca gccaacgact gtgacccatg tgcgccttgc    1380
accgtgctgc ccaacgtttc agacccttgt aatgaccgga gcctgtacag ccatcgcttt    1440
tcctacatgg ggacctatcc tgctcagtac acctatcctg gtggacaaga gtccgacaat    1500
gagagcgtgt gctacggctg gacacatgtg agcgcagacg ccaacaatct gatcgatgcg    1560
gagcgaatca cgcagattcc agctgtgaaa gcgtatcaga ccaatggcaa ggtgatcaaa    1620
ggtcctggat caactggagg agacgtcgtg cagctggttt cggatactgg gcaagacttg    1680
cagaaactac ggattcggat gaagggacaa gcccagaagg gttatcaact ccgcatccga    1740
tacgcttctt ccgtgttcta tcagagtctg accgctgacc gctacgtcaa catcgacggg    1800
agctggacca cagctggagg ttcaaacttt cagctaagac cgacctatag tggtgaatcc    1860
ttgaactaca actcgttcgg ctacgccacc ttgtttacga gtctataccc gactccctac    1920
gaggactggg agattgttct gactagcaat agcatacctc ccatcatcat cgataagatc    1980
gagttcatcc ccattgaagg ttccgtggag gagttcgagg ctaatcaagc tcttgagaaa    2040
gcacgaaaag ccgtgaacac cctgtttact ggtgatgcca gaacgcact taagctgaac    2100 ataaccgatt acgctgtaga tcaagcagcc aatctggctg agtgtgtcag tgaggagttt    2160
cacgcacaag agaagatgat acttcttgac caagtgaagt cgctaagag actctcacat    2220 gcaaggaatc tgctgaacca cggtgatttc gaatccagcg actggtctgg agaaaacggc    2280
tggaaaacat cccctcatgt tcatgttgca gcggaccatc caatcttcaa gggacgctat    2340
ctccacatgc ctggtgccac atcttctccc ttcagcagcc acgtctatcc cacgtacatc    2400
tatcagaagg tggacgaatc caagttgaag tcctacacaa gatacctggt gcgagggttc    2460
gtggggaact ctaaggatct cgaactgctg gtggaacgct acggcaaaga tgtccatgtc    2520
gagttagacg ttcccaacga tatccagtac tctctcccta tgaacgagtg cggaggattt    2580
gacagatgca gacccgtgtt ctatcaagca aggtctagcc acgcgtgtac gtgcaaagac    2640
actgcctcca tgcacacaga ctgtcaatgt aaggacaagg tcaaccgcac ctcagcggac    2700
ggctacacaa atgtccttac tgggtctatg gtttacacaa acgagttcca tgcccacaag    2760
agctgtgggt gcaagaacaa tgatatgtat cagtctggca cacatccgca caagagttgt    2820
ggctgtaaag atccgcacgt gttcacctat cacatagata ctgggtgtgt ggatcaagag    2880
gaaaacgtgg gactgttctt tgctctgaag atcgcatccg agaatggggt ggcgaacatt    2940
gacaacctgg aaatcatcga ggctcagcct ctcactgggg aagcccttgc cagagtgaag    3000
aagcgagagc agaaatggaa gcaagaaatg gagcagaaaa gactgcaaac agagaaagcc    3060
gttcaagcag cacaaggtgc aattcaacct tgtttacga acgctcagta caatcggctc    3120
cagttcgaga cgctgtttcc acagatcgtc agagccgaaa agctggtcca gcaaatccct    3180
tacgtgtatc atccatttct ctccggagcc ttgttagccg tgcctgggat gaacttcgat    3240
atcgtgcagc agctgagtgc cctcgtcgat agagccagag ggctatacga tctgcgaaat    3300
ctcgtgcaga acggaacctt tcaagcggga actggcaact ggcacgtatc agaaggcgta    3360
aaggtccaac ccttacagaa cacatctgtg ctggtcttga gcgagtggaa ccacgaggca    3420
agtcagcagc tgaggattga tccggatcgt ggctatgttc ttagagtaac cgcacggaaa    3480
gaaggagctg gaaaaggcac cgtcactatg agcgactgtg ccgattacac tgaaacctta    3540
acgttcacca gctgcgacta caacaccgta ggttcacaag ccatgacggg tgggacactc    3600
```

```
tctggatttg tgaccaagac actggaaatc tttccagaca ctgaccgtat cagaatagac      3660
attggcgaaa cagaaggcac attcaagatc gaaagcgtag aactgatctg catggaacag      3720
atggagaaca atggg                                                       3735
```

<210> SEQ ID NO 4
<211> LENGTH: 1245
<212> TYPE: PRT
<213> ORGANISM: Artificial Sequence
<220> FEATURE:
<223> OTHER INFORMATION: Maize optimized

<400> SEQUENCE: 4

```
Met Asp Thr Ser Asn Met Gly Tyr Gln Pro Arg Tyr Pro Phe Ala Lys
1               5                   10                  15

Ala Pro Arg Ser Glu Leu Gln Asn Met Asp Tyr Lys Asp Trp Met Asn
            20                  25                  30

Arg Cys Thr Ser Glu Glu Ser Phe Ser Gln Gly Thr Ser Asn Ser Ile
        35                  40                  45

Arg Asp Ala Val Ile Ala Gly Ser Lys Ile Ala Gly Thr Ile Ile Gly
    50                  55                  60

Ala Val Phe Pro Pro Leu Lys Ile Pro Ala Leu Ile Leu Ser Asn Leu
65                  70                  75                  80

Ile Pro Phe Leu Trp Pro Lys Glu Ala Gly Pro Pro Gly Thr Pro Glu
                85                  90                  95

Ala Gln Phe Thr Trp Glu Gln Met Met Asn Ala Val Glu Glu Met Val
            100                 105                 110

Asp Gln Lys Ile Asp Thr Leu Val Lys Asp Gln Ala Ile Ser Thr Leu
        115                 120                 125

Gln Ile Leu Gln Ser Tyr Ile Gln Asp Tyr Gln Ala Leu Cys Asn
    130                 135                 140

Leu Gln Thr Asp Pro Asn Asn Glu Lys Tyr Lys Glu Asp Val Arg Arg
145                 150                 155                 160

Glu Phe Asn Asp Ala Glu Asp Gln Ala Lys Ala Ile Ile Gln Phe
                165                 170                 175

Arg Asn Val Lys Tyr Ala Gly Leu Leu Leu Ala Asp Tyr Ala Gln Ala
            180                 185                 190

Ala Asn Leu His Leu Leu Leu Arg Asp Val Val Gln Phe Gly Glu
        195                 200                 205

Ser Trp Gly Phe Ser Ala Leu Glu Val Gln Gln Tyr Tyr Ser Asn Glu
    210                 215                 220

Ser Leu Val Gly Asn Pro Gly Met Lys Gln Leu Leu Ala Thr Tyr Thr
225                 230                 235                 240

Asp His Cys Val Arg Trp Tyr Asn Glu Gly Leu Gln Asn Arg Tyr Glu
                245                 250                 255

Thr Gly Asn Trp Asn Thr Phe Asn Asp Phe Arg Arg Asn Met Thr Leu
            260                 265                 270

Met Ile Leu Asp Ile Val Ala Ile Trp Pro Thr Tyr Asp Pro Ile Leu
        275                 280                 285

Tyr Thr Val Pro Thr Lys Ser Gln Leu Thr Arg Thr Val Tyr Thr Pro
    290                 295                 300

Phe Ile Gln Gly Ser Leu Ser Ile Lys Pro Leu Thr Ile Ser Val Ile
305                 310                 315                 320

Glu Asn Asn Val Pro Ala Pro Pro Asp Leu Phe Arg Trp Leu Arg Glu
                325                 330                 335
```

```
Ile Ala Phe Tyr Ala Glu Gly Pro Val Ala Pro Gly Ser Arg Val Leu
            340                 345                 350

Ser Gly Gln Ile Gln Arg Tyr Gln Tyr Thr Leu Arg Asp Leu Leu Tyr
            355                 360                 365

Glu Glu Ala Lys Gly Glu Leu Val Glu Gln Val Gly Thr Leu Val Val
370                 375                 380

Pro His Pro Thr Ser Glu Asp Val Trp Ser Leu Leu Met Asn Tyr
385                 390                 395                 400

Ser Lys Ile Asn Tyr Val Pro Tyr Pro Ile Met Ala Gly Leu Asn Tyr
            405                 410                 415

Leu Asp Phe His Leu Thr Lys Thr Val Asp Gln Arg Ile Thr Phe Leu
            420                 425                 430

Pro Asp His Val Ser Arg Asn Glu Thr Phe Gly Leu Pro Cys Gly Pro
            435                 440                 445

Asn Pro Ala Asn Asp Cys Asp Pro Cys Ala Pro Cys Thr Val Leu Pro
450                 455                 460

Asn Val Ser Asp Pro Cys Asn Asp Arg Ser Leu Tyr Ser His Arg Phe
465                 470                 475                 480

Ser Tyr Met Gly Thr Tyr Pro Ala Gln Tyr Thr Tyr Pro Gly Gly Gln
            485                 490                 495

Glu Ser Asp Asn Glu Ser Val Cys Tyr Gly Trp Thr His Val Ser Ala
            500                 505                 510

Asp Ala Asn Asn Leu Ile Asp Ala Glu Arg Ile Thr Gln Ile Pro Ala
            515                 520                 525

Val Lys Ala Tyr Gln Thr Asn Gly Lys Val Ile Lys Gly Pro Gly Ser
            530                 535                 540

Thr Gly Gly Asp Val Val Gln Leu Val Ser Asp Thr Gly Gln Asp Leu
545                 550                 555                 560

Gln Lys Leu Arg Ile Arg Met Lys Gly Gln Ala Gln Lys Gly Tyr Gln
            565                 570                 575

Leu Arg Ile Arg Tyr Ala Ser Ser Val Phe Tyr Gln Ser Leu Thr Ala
            580                 585                 590

Asp Arg Tyr Val Asn Ile Asp Gly Ser Trp Thr Thr Ala Gly Gly Ser
            595                 600                 605

Asn Phe Gln Leu Arg Pro Thr Tyr Ser Gly Glu Ser Leu Asn Tyr Asn
            610                 615                 620

Ser Phe Gly Tyr Ala Thr Leu Phe Thr Ser Leu Tyr Pro Thr Pro Tyr
625                 630                 635                 640

Glu Asp Trp Glu Ile Val Leu Thr Ser Asn Ser Ile Pro Pro Ile Ile
            645                 650                 655

Ile Asp Lys Ile Glu Phe Ile Pro Ile Glu Gly Ser Val Glu Glu Phe
            660                 665                 670

Glu Ala Asn Gln Ala Leu Glu Lys Ala Arg Lys Ala Val Asn Thr Leu
            675                 680                 685

Phe Thr Gly Asp Ala Lys Asn Ala Leu Lys Leu Asn Ile Thr Asp Tyr
            690                 695                 700

Ala Val Asp Gln Ala Ala Asn Leu Ala Glu Cys Val Ser Glu Glu Phe
705                 710                 715                 720

His Ala Gln Glu Lys Met Ile Leu Leu Asp Gln Val Lys Phe Ala Lys
            725                 730                 735

Arg Leu Ser His Ala Arg Asn Leu Leu Asn His Gly Asp Phe Glu Ser
            740                 745                 750
```

```
Ser Asp Trp Ser Gly Glu Asn Gly Trp Lys Thr Ser Pro His Val His
        755                 760                 765

Val Ala Ala Asp His Pro Ile Phe Lys Gly Arg Tyr Leu His Met Pro
770                 775                 780

Gly Ala Thr Ser Ser Pro Phe Ser Ser His Val Tyr Pro Thr Tyr Ile
785                 790                 795                 800

Tyr Gln Lys Val Asp Glu Ser Lys Leu Lys Ser Tyr Thr Arg Tyr Leu
            805                 810                 815

Val Arg Gly Phe Val Gly Asn Ser Lys Asp Leu Glu Leu Leu Val Glu
                820                 825                 830

Arg Tyr Gly Lys Asp Val His Val Glu Leu Asp Val Pro Asn Asp Ile
        835                 840                 845

Gln Tyr Ser Leu Pro Met Asn Glu Cys Gly Gly Phe Asp Arg Cys Arg
    850                 855                 860

Pro Val Phe Tyr Gln Ala Arg Ser Ser His Ala Cys Thr Cys Lys Asp
865                 870                 875                 880

Thr Ala Ser Met His Thr Asp Cys Gln Cys Lys Asp Lys Val Asn Arg
            885                 890                 895

Thr Ser Ala Asp Gly Tyr Thr Asn Val Leu Thr Gly Ser Met Val Tyr
                900                 905                 910

Thr Asn Glu Phe His Ala His Lys Ser Cys Gly Cys Lys Asn Asn Asp
        915                 920                 925

Met Tyr Gln Ser Gly Thr His Pro Lys Ser Cys Gly Cys Lys Asp
    930                 935                 940

Pro His Val Phe Thr Tyr His Ile Asp Thr Gly Cys Val Asp Gln Glu
945                 950                 955                 960

Glu Asn Val Gly Leu Phe Phe Ala Leu Lys Ile Ala Ser Glu Asn Gly
            965                 970                 975

Val Ala Asn Ile Asp Asn Leu Glu Ile Ile Glu Ala Gln Pro Leu Thr
                980                 985                 990

Gly Glu Ala Leu Ala Arg Val Lys  Lys Arg Glu Gln Lys  Trp Lys Gln
        995                 1000                 1005

Glu Met Glu Gln Lys Arg Leu  Gln Thr Glu Lys Ala  Val Gln Ala
    1010                1015                1020

Ala Gln Gly Ala Ile Gln Pro  Leu Phe Thr Asn Ala  Gln Tyr Asn
    1025                1030                1035

Arg Leu Gln Phe Glu Thr Leu  Phe Pro Gln Ile Val  Arg Ala Glu
    1040                1045                1050

Lys Leu Val Gln Gln Ile Pro  Tyr Val Tyr His Pro  Phe Leu Ser
    1055                1060                1065

Gly Ala Leu Leu Ala Val Pro  Gly Met Asn Phe Asp  Ile Val Gln
    1070                1075                1080

Gln Leu Ser Ala Leu Val Asp  Arg Ala Arg Gly Leu  Tyr Asp Leu
    1085                1090                1095

Arg Asn Leu Val Gln Asn Gly  Thr Phe Ser Ser Gly  Thr Gly Asn
    1100                1105                1110

Trp His Val Ser Glu Gly Val  Lys Val Gln Pro Leu  Gln Asn Thr
    1115                1120                1125

Ser Val Leu Val Leu Ser Glu  Trp Asn His Glu Ala  Ser Gln Gln
    1130                1135                1140

Leu Arg Ile Asp Pro Asp Arg  Gly Tyr Val Leu Arg  Val Thr Ala
    1145                1150                1155

Arg Lys Glu Gly Ala Gly Lys  Gly Thr Val Thr Met  Ser Asp Cys
```

```
                    1160                1165                1170
Ala Asp Tyr Thr Glu Thr Leu Thr Phe Thr Ser Cys Asp Tyr Asn
    1175                1180                1185

Thr Val Gly Ser Gln Ala Met Thr Gly Gly Thr Leu Ser Gly Phe
    1190                1195                1200

Val Thr Lys Thr Leu Glu Ile Phe Pro Asp Thr Asp Arg Ile Arg
    1205                1210                1215

Ile Asp Ile Gly Glu Thr Glu Gly Thr Phe Lys Ile Glu Ser Val
    1220                1225                1230

Glu Leu Ile Cys Met Glu Gln Met Glu Asn Asn Gly
    1235                1240                1245
```

DIG-303 INSECTICIDAL CRY TOXINS

CROSS REFERENCE

This application claims the benefit of U.S. Provisional Application No. 62/073,649, filed Oct. 31, 2014. The disclosure of which is expressly incorporated herein entirely.

BACKGROUND OF THE DISCLOSURE

*Bacillus thuringiensis* (*B.t.*) is a soil-borne bacterium that produces pesticidal crystal proteins known as delta endotoxins or Cry proteins. Cry proteins are oral intoxicants that function by acting on midgut cells of susceptible insects. Some Cry toxins have been shown to have activity against nematodes. An extensive list of delta endotoxins is maintained and regularly updated at the *Bacillus thuringiensis* Toxin Nomenclature web site maintained by Neil Crickmore. (See Crickmore et al. 1998, page 808).

Coleopterans are a significant group of agricultural pests that cause extensive damage to crops each year. Examples of coleopteran pests include Colorado potato beetle (CPB), corn rootworm, alfalfa weevil, boll weevil, and Japanese beetle. The Colorado potato beetle is an economically important pest that feeds on the leaves of potato, eggplant, tomato, pepper, tobacco, and other plants in the nightshade family. The Colorado potato beetle is a problematic defoliator of potatoes, in part, because it has developed resistance to many classes of insecticides. Cry toxins, including members of the Cry3, Cry7, and Cry8 families have insecticidal activity against coleopteran insects.

Although production of the currently-deployed Cry proteins in transgenic plants can provide robust protection against the aforementioned pests, thereby protecting grain yield, adult pests have emerged in artificial infestation trials, indicating less than complete larval insect control. Additionally, development of resistant insect populations threatens the long-term durability of Cry proteins in insect pest control. Lepidopteran insects resistant to Cry proteins have developed in the field for *Plutella xylostella* (Tabashnik, 1994), *Trichoplusia ni* (Janmaat and Myers, 2003, 2005), and *Helicoverpa zea* (Tabashnik et al., 2008). Coleopteran insects likewise have developed resistance in the field to Cry proteins (Gassman et al. PLoS ONE July 2011|Volume 6|Issue 7|e22629). Insect resistance to *B.t.* Cry proteins can develop through several mechanisms (Heckel et al., 2007; Pigott and Ellar, 2007). Multiple receptor protein classes for Cry proteins have been identified within insects, and multiple examples exist within each receptor class. Resistance to a particular Cry protein may develop, for example, by means of a mutation within the toxin-binding portion of a cadherin domain of a receptor protein. A further means of resistance may be mediated through a protoxin-processing protease.

There is interest in the development of new Cry proteins that provide additional tools for management of coleopteran insect pests. Cry proteins with different modes of action produced in combination in transgenic plants would prevent the development of insect resistance and protect the long term utility of *B.t.* technology for insect pest control.

BRIEF SUMMARY OF THE DISCLOSURE

The present invention is based on the discovery of insecticidal toxins based on the Cry protein toxin designated herein as DIG-303, including variants of DIG-303, nucleic acids encoding these toxins, methods of controlling pests using the toxins, methods of producing the toxins in transgenic host cells, and transgenic plants that express the toxins. The amino acid sequence of native DIG-303 toxin in SEQ ID NO:2 indicates that DIG-303 is best classified to the Cry32 family.

As described in Example 1, a nucleic acid encoding the DIG-303 protein was discovered and isolated from a *B.t.* strain herein designated as PS18A also known as DBt10340. The nucleic acid sequence for the full length coding region was determined, and the full length protein sequence was deduced from the nucleic acid sequence. The nucleic acid sequence encoding DIG-303 toxin is given in SEQ ID NO:1. A BLAST search using the insecticidal core fragment as a query found that DIG-303 toxin protein has less than 60% sequence identity to the core fragment of the closest Cry toxin known at the time of the search (AAG36711) and less than 70% homology to the closest publically disclosed sequence (Axmil74 ATX25337). Thus, DIG-303 represents a new subclass within the Cry32 family of proteins.

The DIG-303 toxins can be used alone or in combination with other Cry toxins, such as Cry34Ab1/Cry35Ab1 (Event DAS-59122-7), Cry3Bb1 (event MON88017), Cry3A (event MIR604), chimeric Cry3A/Cry1Ab (eCry3.1Ab, FR8A, Event 5307, WO 2008/121633 A1), CryET33 and CryET34, Vip1A, Cry1Ia, CryET84, CryET80, CryET76, CryET71, CryET69, CryET75, CryET39, CryET79, TIC809, TIC810, and CryET74 to control the development of resistant Coleopteran insect populations. Further, DIG-303 toxins can be used alone or in combination with other Cry toxins that control the development of other pest populations, such as, for example, Cry1F, Cry1Ab, Vip3A, Cry2A, Cry1Da, Cry1Ia, and Cry1Ac to control the development of lepidopteran resistant insect populations.

DIG-303 insecticidal toxins may also be used in combination with RNAi methodologies for control of other insect pests. For example, DIG-303 insecticidal toxins can be used in transgenic plants in combination with a dsRNA for suppression of an essential gene in CPB, corn rootworm or another insect pest. Such target genes include, for example, ATPase encoding genes in CPB. Other such target genes include, for example, vacuolar ATPase, ARF-1, Act42A, CHD3, EF-1α, ROP, RNAPII, and TFIIB in corn rootworm. An example of a suitable target gene is vacuolar ATPase, as disclosed in WO2007035650.

In one embodiment, the invention provides an isolated, treated, or formulated DIG-303 insecticidal toxin polypeptide comprising a core toxin segment selected from the group consisting of
  (a) the amino acid sequence of residues from approximately 1 to approximately 685 of SEQ ID NO:2;
  (b) an amino acid sequence having at least 70% sequence identity to the amino acid sequence of residues from approximately 1 to approximately 685 of SEQ ID NO:2;
  (c) an amino acid sequence having at least 80% sequence identity to the amino acid sequence of residues from approximately 1 to approximately 685 of SEQ ID NO:2;
  (d) an amino acid sequence having at least 90% sequence identity to the amino acid sequence of residues from approximately 1 to approximately 685 of SEQ ID NO:2;
  (e) an amino acid sequence having at least 95% sequence identity to the amino acid sequence of residues from approximately 1 to approximately 685 of SEQ ID NO:2;

(f) an amino acid sequence having at least 99% sequence identity to the amino acid sequence of residues from approximately 1 to approximately 685 of SEQ ID NO:2; and (g) an amino acid sequence of residues from approximately 1 to approximately 685 of SEQ ID NO:2, with up to 20 amino acid substitutions, deletions, or modifications that do not adversely affect expression or activity of the toxin of SEQ ID NO:2; or an insecticidal active fragment of either (a), (b), (c), (d), (e), (f) and (g).

In further embodiments, the DIG-303 insecticidal toxin polypeptides described above can be linked to a C-terminal protoxin segment of a different cry toxin, e.g. the C-terminal region of a different cry toxin in which the core toxin segment has been removed. In particular, the C-terminal protoxin segment of Cry1Ab or Cry1Ac/Cry1Ab chimeric toxin are well known in the art to aid the stable expression of chimeric cry core toxins.

In another embodiment the invention provides a purified, treated, or formulated DIG-303 insecticidal toxin having substantially different properties than the native toxin has in its natural state comprising a DIG-303 core toxin segment selected from the group consisting of a (a) polypeptide comprising the amino acid sequence of residues 1 to 1257 of SEQ ID NO:2; (b) polypeptide comprising an amino acid sequence having at least 90% sequence identity to the amino acid sequence of residues 1 to 1257 of SEQ ID NO:2; and (c) polypeptide comprising an amino acid sequence of residues 1 to 1257 of SEQ ID NO:2, with up to 20 amino acid substitutions, deletions, or modifications that do not adversely affect expression or activity of the toxin of SEQ ID NO:2; or an insecticidal active fragment of either (a), (b), or (c).

In another embodiment the invention provides a transgenic plant comprising a DIG-303 insecticidal toxin.

In another embodiment the invention provides a method for controlling a pest population comprising contacting individuals of said population with a pesticidally effective amount of a DIG-303 insecticidal toxin.

In another embodiment the invention provides a non-naturally occurring nucleic acid that encodes a DIG-303 insecticidal toxin.

In another embodiment the invention provides a DNA construct comprising a nucleotide sequence that encodes a DIG-303 insecticidal toxin operably linked to a heterologous promoter and is capable of driving expression in a plant. The invention also provides a transgenic plant that comprises the DNA construct stably incorporated into its genome and a method for protecting a plant from a pest comprising expression of the construct in said plant.

By "isolated" or "purified" applicants mean that the nucleotide or polypeptide molecules have been removed from their native environment and have been placed in a different environment by the hand of man. Thus, isolated nucleotide and polypeptide molecules include DNA or protein molecules that have been purified, concentrated, or otherwise rendered substantially free of *Bacillus thuringiensis* cellular material. Embodiments of isolated DIG-303 insecticidal polypeptide or nucleotide molecules can have less than about 30%, less than about 20%, less than about 10%, less than about 9%, less than about 8%, less than about 7%, less than about 6%, less than about 5%, less than about 4%, less than about 3% or less than about 2%, or less than about 1% (by dry weight) of contaminating protein (e.g., from *Bacillus thuringiensis*). When the isolated DIG-303 insecticidal polypeptide or nucleotide embodiments is recombinantly produced, then the culture medium material, chemical precursors, and/or or non-DIG-303 insecticidal polypeptide or nucleotide represent less than about 30%, less than about 20%, less than about 10%, less than about 5%, less than about 4%, less than about 3% or less than about 2%, or less than about 1% (by dry weight) of the isolated DIG-303 insecticidal polypeptide or nucleotide.

BRIEF DESCRIPTION OF THE SEQUENCES

SEQ ID NO:1 shows DNA encoding DIG-303 toxins with 10 variable nucleotides; 3771 nt.

SEQ ID NO:2 shows DIG-303 protein sequences having 10 variable amino acid residues; 1257 aa.

SEQ ID NO:3 is a maize-optimized DNA sequence encoding a DIG-303 toxin in which the 36 5' nucleotides are deleted; 3735 nt.

SEQ ID NO:4 is the DIG-303 protein sequence encoded by SEQ ID NO:3 in which the 12 N-terminal amino acid residue were deleted. 1245 aa

DETAILED DESCRIPTION OF THE DISCLOSURE

DIG-303 Insecticidal Toxins:

In addition to the full length DIG-303 toxin of SEQ ID NO:2, the invention encompasses insecticidal active variants thereof. By the term "variant", applicants intend to include fragments, certain deletion and insertion mutants, and certain fusion or chimeric proteins. DIG-303 includes three-domains generally associated with a Cry toxin. As a preface to describing variants of the DIG-303 toxin that are included in the invention, it will be useful to briefly review the architecture of three-domain Cry toxins in general and of the DIG-303 protein toxin in particular.

A majority of *Bacillus thuringiensis* delta-endotoxin crystal protein molecules are composed of two functional segments. The protease-resistant core toxin is the first segment and corresponds to about the first half of the protein molecule. The full ~130 kDa protoxin molecule is rapidly processed to the resistant core segment by proteases in the insect gut. The C-terminal segment that is deleted by this enzymatic processing will be referred to herein as the "C-terminal protoxin segment." The C-terminal protoxin segment is believed to participate in toxin crystal formation (Arvidson et al., 1989). The C-terminal protoxin segment may thus convey a partial insect specificity for the toxin by limiting the accessibility of the core to the insect by reducing the protease processing of the toxin molecule (Haider et al., 1986) or by reducing toxin solubility (Aronson et al., 1991). *B.t.* toxins, even within a certain class, vary to some extent in length and in the precise location of the transition from the core toxin segment to C-terminal protoxin segment. The transition from core toxin segment to C-terminal protoxin segment will typically occur at between about 50% to about 60% of the full length toxin. SEQ ID NO:2 discloses the 1257 amino acid sequence of the partial DIG-303 polypeptide, of which the N-terminal 685 amino acids comprise a DIG-303 core toxin segment.

Three dimensional crystal structures have been determined for Cry1Aa1, Cry2Aa1, Cry3Aa1, Cry3Bb1, Cry4Aa, Cry4Ba and Cry8Ea1. These structures for the core toxins are remarkably similar and are comprised of three distinct domains with the features described below (reviewed in de Maagd et al., 2003).

Domain I is a bundle of seven alpha helices where helix five is surrounded by six amphipathic helices. This domain has been implicated in pore formation and shares homology with other pore forming proteins including hemolysins and colicins. Domain I of the DIG-303 protein comprises amino acid residues approximately 1-300 of SEQ ID NO:2.

Domain II is formed by three anti-parallel beta sheets packed together in a beta prism. The loops of this domain play important roles in binding insect midgut receptors. In Cry1A proteins, surface exposed loops at the apices of Domain II beta sheets are involved in binding to Lepidopteran cadherin receptors. Cry3Aa Domain II loops bind a membrane-associated metalloprotease of *Leptinotarsa decemlineata* Say (CPB) in a similar fashion (Ochoa-Campuzano et al., 2007). Domain II shares homology with certain carbohydrate-binding proteins including vitelline and jacaline. Domain II of the DIG-303 protein comprises amino acid residues approximately 300-525 of SEQ ID NO:2.

Domain III is a beta sandwich of two anti-parallel beta sheets. Structurally this domain is related to carbohydrate-binding domains of proteins such as glucanases, galactose oxidase, sialidase, and others.

Conserved *B.t.* sequence blocks 2 and 3 map near the N-terminus and C-terminus of Domain 2, respectively. Hence, these conserved sequence blocks 2 and 3 are approximate boundary regions between the three functional domains. These regions of conserved DNA and protein homology have been exploited for engineering recombinant *B.t.* toxins (U.S. Pat. No. 6,090,931, WP1991001087, WO1995006730, U.S. Pat. Nos. 5,736,131, 6,204,246, 6,780,408, WO1998022595, US Patent Application No. 20090143298, and U.S. Pat. No. 7,618,942). Domain III of the DIG-303 protein comprises amino acid residues approximately 526-685 of SEQ ID NO:2.

In lepidotperan insects it has been reported that Cry1A toxins bind certain classes of receptor proteins including cadherins, aminopeptidases and alkaline phosphatases, others remain to be identified (Honée et al., 1991; Pigott and Ellar, 2007). In coleopteran insects, two receptors have been identified for Cry3Aa; in Colorado potato beetle an ADAM metalloprotease (Ochoa-Campuzano et al., 2007), in Tenebrio a cadherin has been identified (Fabrick et al., 2009). Given the diversity of *Bacillus thuringiensis* toxins and pests it is anticipated that additional receptors will be identified that will include additional classes of proteins and membrane surface substituents.

It has been reported that α-helix 1 of Domain I is removed following receptor binding. Aronson et al. (1999) demonstrated that Cry1Ac bound to brush border membrane vesicles (BBMV) was protected from proteinase K cleavage beginning at residue 59, just after α-helix 1; similar results were cited for Cry1Ab. Gomez et al. (2002) found that Cry1Ab oligomers formed upon BBMV receptor binding lacked the α-helix 1 portion of Domain I. Also, Soberon et al. (2007) have shown that N-terminal deletion mutants of Cry1Ab and Cry1Ac which lack approximately 60 amino acids encompassing α-helix 1 on the three dimensional Cry structure are capable of assembling monomers of molecular weight about 60 kDa into pre-pores in the absence of cadherin binding. These N-terminal deletion mutants were reported to be active on Cry-resistant insect larvae. Furthermore, Diaz-Mendoza et al. (2007) described Cry1Ab fragments of 43 kDa and 46 kDa that retained activity on Mediterranean corn borer (*Sesamia nonagrioides*). These fragments were demonstrated to include amino acid residues 116 to 423 of Cry1Ab; however the precise amino acid sequences were not elucidated and the mechanism of activity of these proteolytic fragments is unknown. The results of Gomez et al. (2002), Soberon et al. (2007) and Diaz-Mendoza et al. (2007) contrast with those of Hofte et al. (1986), who reported that deletion of 36 amino acids from the N-terminus of Cry1Ab resulted in loss of insecticidal activity.

Amino Terminal Deletion Variants of DIG-303:

In one of its aspects, the invention provides DIG-303 variants in which all or part of one or more α-helices are deleted to improve insecticidal activity and avoid development of resistance by insects. These modifications are made to provide DIG-303 variants with improved attributes, such as improved target pest spectrum, potency, and insect resistance management. In some embodiments of the subject invention, the subject modifications may affect the efficiency of full length protoxin activation and pore formation, leading to insect intoxication. More specifically, to provide DIG-303 variants with improved attributes, step-wise deletions are described that remove part of the DNA sequence encoding the N-terminus Such deletions remove all of α-helix 1 and all or part of α-helix 2 in Domain I, while maintaining the structural integrity of the α-helices 3 through 7. The subject invention therefore relates in part to improvements to Cry protein efficacy made by engineering the α-helical components of Domain I for more efficient pore formation. More specifically, the subject invention provides improved DIG-303 proteins designed to have N-terminal deletions in regions with putative secondary structure homology to α-helices 1 and 2 in Domain I of Cry1 proteins.

In designing coding sequences for the N-terminal deletion variants, an ATG start codon, encoding methionine, is inserted at the 5' end of the nucleotide sequence designed to express the deletion variant. For sequences designed for use in transgenic plants, it may be of benefit to adhere to the "N-end rule" of Varshavsky (1997). It is taught that some amino acids may contribute to protein instability and degradation in eukaryotic cells when displayed as the N-terminal residue of a protein. For example, data collected from observations in yeast and mammalian cells indicate that the N-terminal destabilizing amino acids are F, L, W, Y, R, K, H, I, N, Q, D, E and possibly P. While the specifics of protein degradation mechanisms may differ somewhat between organisms, the conservation of identity of N-terminal destabilizing amino acids seen above suggests that similar mechanisms may function in plant cells. For instance, Worley et al. (1998) found that in plants the N-end rule includes basic and aromatic residues. It may be that proteolytic cleavage by plant proteases near the start of α-helix 3 of subject *B.t.* insecticidal proteins expose a destabilizing N-terminal amino acid. Such processing may target the cleaved proteins for rapid decay and limit the accumulation of the *B.t.* insecticidal proteins to levels insufficient for effective insect control. Accordingly, for certain examples of N-terminal deletion variants that begin with one of the destabilizing amino acids, a codon that specifies a G (glycine) amino acid can be added between the translational initiation methionine and the destabilizing amino acid.

Protease Sensitivity Variants

Insect gut proteases typically function in aiding the insect in obtaining needed amino acids from dietary protein. The best understood insect digestive proteases are serine proteases, which appear to be the most common type (Englemann and Geraerts, 1980), particularly in lepidopteran species. Coleopteran insects have guts that are more neutral to acidic than are lepidopteran guts. The majority of coleopteran larvae and adults, for example CPB, have slightly acidic midguts, and cysteine proteases provide the major proteolytic activity (Wolfson and Murdock, 1990). More precisely, Thie and Houseman (1990) identified and characterized the cysteine proteases, cathepsin B-like and cathepsin H-like, and the aspartyl protease, cathepsin D-like, in CPB. Gillikin et al. (1992) characterized the proteolytic activity in the guts of western corn rootworm larvae and found primarily cysteine proteases. U.S. Pat. No. 7,230,167 disclosed that a protease activity attributed to cathepsin G exists in western corn rootworm. The diversity and different activity levels of the insect gut proteases may influence an insect's sensitivity to a particular *B.t.* toxin.

In another embodiment of the invention, protease cleavage sites may be engineered at desired locations to affect protein processing within the midgut of susceptible larvae of certain insect pests. These protease cleavage sites may be introduced by methods such as chemical gene synthesis or splice overlap PCR (Horton et al., 1989). Serine protease recognition sequences, for example, can optionally be inserted at specific sites in the Cry protein structure to affect protein processing at desired deletion points within the midgut of susceptible larvae. Serine proteases that can be exploited in such fashion include lepidopteran midgut serine proteases such as trypsin or trypsin-like enzymes, chymotrypsin, elastase, etc. (Christeller et al., 1992). Further, deletion sites identified empirically by sequencing Cry protein digestion products generated with unfractionated larval midgut protease preparations or by binding to brush border membrane vesicles can be engineered to effect protein activation. Modified Cry proteins generated either by gene deletion or by introduction of protease cleavage sites have improved activity on lepidopteran pests such as *Ostrinia nubilalis, Diatraea grandiosella, Helicoverpa zea, Agrotis ipsilon, Spodoptera frugiperda, Spodoptera exigua, Diatraea saccharalis, Loxagrotis albicosta*, and coleopteran pests such as western corn rootworm, southern corn rootworm, northern corn rootworm (i.e. *Diabrotica* spp.), and other target pests.

Serine proteases of the same family such as trypsin, chymotrypsin and cathepsin G-like protease, coleopteran cysteine proteases such as cathepsins (B-like, L-like, O-like, and K-like proteases) (Koiwa et al., 2000; and Bown et al., 2004), coleopteran metalloproteases such as ADAM10 (Ochoa-Campuzano et al., 2007), and coleopteran aspartic acid proteases such as cathepsins D-like and E-like, pepsin, plasmepsin, and chymosin may further be exploited by engineering appropriate recognition sequences at desired processing sites to affect Cry protein processing within the midgut of susceptible larvae of certain insect pests.

A preferred location for the introduction of such protease cleavage sites is within the "spacer" region between α-helix2B and α-helix3. A second preferred location for the introduction of protease cleavage sites is within the spacer region between α-helix3 and α-helix4. Modified DIG-303 insecticidal toxin proteins are generated either by gene deletion or by introduction of protease cleavage sites to provide improved activity on insect pests including but not limited Colorado potato beetle (CPB), corn rootworm, alfalfa weevil, boll weevil, and Japanese beetle, and the like.

Various technologies exist to enable determination of the sequence of the amino acids which comprise the N-terminal or C-terminal residues of polypeptides. For example, automated Edman degradation methodology can be used in sequential fashion to determine the N-terminal amino acid sequence of up to 30 amino acid residues with 98% accuracy per residue. Further, determination of the sequence of the amino acids comprising the carboxy end of polypeptides is also possible (Bailey et al., 1992; U.S. Pat. No. 6,046,053).

Thus, in some embodiments, *B.t.* Cry proteins which have been activated by means of proteolytic processing, for example, by proteases prepared from the gut of an insect, may be characterized and the N-terminal or C-terminal amino acids of the activated toxin fragment identified. DIG-303 variants produced by introduction or elimination of protease processing sites at appropriate positions in the coding sequence to allow, or eliminate, proteolytic cleavage of a larger variant protein by insect, plant or microorganism proteases are within the scope of the invention. The end result of such manipulation is understood to be the generation of toxin fragment molecules having the same or better activity as the intact (full length) toxin protein.

Domains of the DIG-303 Toxin:

The separate domains of the DIG-303 toxin, (and variants that are 90%, 91%, 92%, 93, 94%, 95%, 96%, 97%, 98%, or 99% identical to such domains) are expected to be useful in forming combinations with domains from other Cry toxins to provide new toxins with increased spectrum of pest toxicity, improved potency, or increased protein stability. Domain I of the DIG-303 protein comprises approximately amino acid residues 1 to 300 of SEQ ID NO:2. Domain II of the DIG-303 protein comprises approximately amino acid residues 301 to 525 of SEQ ID NO:2. Domain III of the DIG-303 protein comprises approximately amino acid residues 526 to 685 of SEQ ID NO:2. Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Domain II is involved in receptor binding, and Domain III binds certain classes of receptor proteins and perhaps participates in insertion of an oligomeric toxin pre-pore. Some Domain III substitutions in other toxins have been shown to produce superior toxicity against *Spodoptera exigua* (de Maagd et al., 1996) and guidance exists on the design of the Cry toxin domain swaps (Knight et al., 2004).

Methods for generating recombinant proteins and testing them for pesticidal activity are well known in the art (see, for example, Naimov et al., 2001; de Maagd et al., 1996; Ge et al., 1991; Schnepf et al., 1990; Rang et al., 1999). Domain I from Cry1A and Cry3A proteins has been studied for the ability to insert and form pores in membranes. α-helices 4 and 5 of Domain I play key roles in membrane insertion and pore formation (Walters et al., 1993; Gazit et al., 1998; Nunez-Valdez et al., 2001), with the other helices proposed to contact the membrane surface like the ribs of an umbrella (Bravo et al., 2007; Gazit et al., 1998).

DIG-303 Variants Created by Making a Limited Number of Amino Acid Deletions, Substitutions, or Additions:

Amino acid deletions, substitutions, and additions to the amino acid sequence of SEQ ID NO:2 can readily be made in a sequential manner and the effects of such variations on insecticidal activity can be tested by bioassay. Provided the number of changes is limited in number, such testing does not involve unreasonable experimentation. The invention includes insecticidal active variants of the core toxin (approximately amino acids 1 to 685 of SEQ ID NO:2), in which up to 10, up to 15, or up to 20 amino acid additions, deletions, or substitutions have been made.

The invention includes DIG-303 insecticidal toxin variants having a core toxin segment that is 90%, 91%, 92%, 93, 94%, 95%, 96%, 97%, 98%, or 99% identical to amino acids 1 to 685 of SEQ ID NO:2. Variants may be made by making random mutations or the variants may be designed. In the case of designed mutants, there is a high probability of generating variants with similar activity to the native toxin when amino acid identity is maintained in critical regions of the toxin which account for biological activity or are involved in the determination of three-dimensional configuration which ultimately is responsible for the biological activity. A high probability of retaining activity will also occur if substitutions are conservative. Amino acids may be placed in the following classes: non-polar, uncharged polar, basic, and acidic. Conservative substitutions whereby an amino acid of one class is replaced with another amino acid of the same type are least likely to materially alter the biological activity of the variant. Table 1 provides a listing of examples of amino acids belonging to each class.

TABLE 1

| Class of Amino Acid | Examples of Amino Acids |
| --- | --- |
| Nonpolar Side Chains | Ala, Val, Leu, Ile, Pro, Met, Phe, Trp |
| Uncharged Polar Side Chains | Gly, Ser, Thr, Cys, Tyr, Asn, Gln |
| Acidic Side Chains | Asp, Glu |
| Basic Side Chains | Lys, Arg, His |
| Beta-branched Side Chains | Thr, Val, Ile |
| Aromatic Side Chains | Tyr, Phe, Trp, His |

In some instances, non-conservative substitutions can also be made. The critical factor is that these substitutions must not significantly detract from the biological activity of the toxin. Variants include polypeptides that differ in amino acid sequence due to mutagenesis. Variant proteins encompassed by the present invention are biologically active, that is they continue to possess the desired biological activity of the native protein, that is, retaining pesticidal activity.

Variant proteins can also be designed that differ at the sequence level but that retain the same or similar overall essential three-dimensional structure, surface charge distribution, and the like. See, for example, U.S. Pat. No. 7,058,515; Larson et al. (2002); Stemmer (1994a, 1994b, 1995) and Crameri et al. (1996a, 1996b, 1997). U.S. Pat. No. 8,513,492 B2

Nucleic Acids:

Isolated nucleic acids encoding DIG-303 insecticidal toxins are one aspect of the present invention. This includes nucleic acids encoding SEQ ID NO:2 and complements thereof, as well as other nucleic acids that encode insecticidal variants of SEQ ID NO:2. The term "isolated" is defined herein above. Because of the redundancy of the genetic code, a variety of different DNA sequences can encode the amino acid sequences disclosed herein. It is well within the skill of a person trained in the art to create these alternative DNA sequences encoding the same, or essentially the same, toxins.

Gene Synthesis:

Genes encoding the DIG-303 insecticidal toxins described herein can be made by a variety of methods well-known in the art. For example, synthetic gene segments and synthetic genes can be made by phosphite tri-ester and phosphoramidite chemistry (Caruthers et al., 1987), and commercial vendors are available to perform gene synthesis on demand. Full-length genes can be assembled in a variety of ways including, for example, by ligation of restriction fragments or polymerase chain reaction assembly of overlapping oligonucleotides (Stewart and Burgin, 2005). Further, terminal gene deletions can be made by PCR amplification using site-specific terminal oligonucleotides.

Nucleic acids encoding DIG-303 insecticidal toxins can be made for example, by synthetic construction by methods currently practiced by any of several commercial suppliers. (e.g. U.S. Pat. No. 7,482,119). These genes, or portions or variants thereof, may also be constructed synthetically, for example, by use of a gene synthesizer and the design methods of, for example, U.S. Pat. No. 5,380,831. Alternatively, variations of synthetic or naturally occurring genes may be readily constructed using standard molecular biological techniques for making point mutations. Fragments of these genes can also be made using commercially available exonucleases or endonucleases according to standard procedures. For example, enzymes such as Bal31 or site-directed mutagenesis can be used to systematically cut off nucleotides from the ends of these genes. Also, gene fragments which encode active toxin fragments may be obtained using a variety of restriction enzymes.

Given the amino acid sequence for a DIG-303 insecticidal toxin, a coding sequence can be designed by reverse translating the coding sequence using synonymous codons preferred by the intended host, and then refining the sequence using alternative synonymous codons to remove sequences that might cause problems in transcription, translation, or mRNA stability. Further, synonymous codons may be employed to introduce stop codons in the non-DIG-303 reading frames (i.e. reading frames 2, 3, 4, 5 and 6) to eliminate spurious long open reading frames.

Quantifying Polypeptide or Nucleic Acid Sequence Identity:

The percent identity of two amino acid sequences or of two nucleic acid sequences is determined by first aligning the sequences for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of such an algorithm is that of Altschul et al. (1990), and Karlin and Altschul (1990), modified as in Karlin and Altschul (1993), and incorporated into the BLASTN and BLASTX programs. BLAST searches may be conveniently used to identify sequences homologous (similar) to a query sequence in nucleic or protein databases. BLASTN searches can be performed, (score=100, word length=12) to identify nucleotide sequences having homology to claimed nucleic acid molecules of the invention. BLASTX searches can be performed (score=50, word length=3) to identify amino acid sequences having homology to claimed insecticidal protein molecules of the invention.

Gapped BLAST (Altschul et al., 1997) can be utilized to obtain gapped alignments for comparison purposes. Alternatively, PSI-Blast can be used to perform an iterated search that detects distant relationships between molecules (Altschul et al., 1997). When utilizing BLAST, Gapped BLAST, and PSI-Blast programs, the default parameters of the respective programs can be used. See www.ncbi.nlm.nih.gov.

A non-limiting example of a mathematical algorithm utilized for the comparison of sequences is the ClustalW algorithm (Thompson et al., 1994). ClustalW compares sequences and aligns the entirety of the amino acid or DNA sequence, and thus can provide data about the sequence conservation of the entire amino acid sequence or nucleotide sequence. The ClustalW algorithm is used in several commercially available DNA/amino acid analysis software packages, such as the ALIGNX module of the Vector NTI Program Suite (Invitrogen, Inc., Carlsbad, Calif.). When aligning amino acid sequences with ALIGNX, one may conveniently use the default settings with a Gap open penalty of 10, a Gap extend penalty of 0.1 and the blosum63mt2 comparison matrix to assess the percent amino acid similarity (consensus) or identity between the two sequences. When aligning DNA sequences with ALIGNX, one may conveniently use the default settings with a Gap open penalty of 15, a Gap extend penalty of 6.6 and the swgapdnamt comparison matrix to assess the percent identity between the two sequences.

Another non-limiting example of a mathematical algorithm utilized for the comparison of sequences is that of Myers and Miller (1988). Such an algorithm is incorporated into the wSTRETCHER program, which is part of the wEMBOSS sequence alignment software package. wSTRETCHER calculates an optimal global alignment of two sequences using a modification of the classic dynamic programming algorithm which uses linear space. The substitution matrix, gap insertion penalty and gap extension penalties used to calculate the alignment may be specified. When utilizing the wSTRETCHER program for comparing nucleotide sequences, a Gap open penalty of 16 and a Gap extend penalty of 4 can be used with the scoring matrix file EDNAFULL. When used for comparing amino acid sequences, a Gap open penalty of 12 and a Gap extend penalty of 2 can be used with the EBLOSUM62 scoring matrix file.

A further non-limiting example of a mathematical algorithm utilized for the comparison of sequences is that of Needleman and Wunsch (1970), which is incorporated in the sequence alignment software packages GAP Version 10 and wNEEDLE. GAP Version 10 may be used to determine sequence identity or similarity using the following parameters: for a nucleotide sequence, % identity and % similarity are found using GAP Weight of 50 and Length Weight of 3, and the nwsgapdna. cmp scoring matrix. For amino acid sequence comparison, % identity or % similarity are determined using GAP weight of 8 and length weight of 2, and the BLOSUM62 scoring program.

wNEEDLE reads two input sequences, finds the optimum alignment (including gaps) along their entire length, and writes their optimal global sequence alignment to file. The algorithm explores all possible alignments and chooses the best, using a scoring matrix that contains values for every possible residue or nucleotide match. wNEEDLE finds the alignment with the maximum possible score, where the score of an alignment is equal to the sum of the matches taken from the scoring matrix, minus penalties arising from opening and extending gaps in the aligned sequences. The substitution matrix and gap opening and extension penalties are user-specified. When amino acid sequences are compared, a default Gap open penalty of 10, a Gap extend penalty of 0.5, and the EBLOSUM62 comparison matrix are used. When DNA sequences are compared using wNEEDLE, a Gap open penalty of 10, a Gap extend penalty of 0.5, and the EDNAFULL comparison matrix are used.

Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by ALIGNX, wNEEDLE, or wSTRETCHER. The % identity is the percentage of identical matches between the two sequences over the reported aligned region (including any gaps in the length) and the % similarity is the percentage of matches between the two sequences over the reported aligned region (including any gaps in the length). Alignment may also be performed manually by inspection.

Recombinant Hosts:

The toxin-encoding genes of the subject invention can be introduced into a wide variety of microbial or plant hosts. Expression of the toxin gene results, directly or indirectly, in the intracellular production and maintenance of the pesticidal protein. With suitable microbial hosts, e.g. *Pseudomonas*, the microbes can be applied to the environment of the pest, where they will proliferate and be ingested. The result is a control of the pest. Alternatively, the microbe hosting the toxin gene can be treated under conditions that prolong the activity of the toxin and stabilize the recombinant host cell. The treated cell, which comprises a treated toxin polypetide of the invention that retains the insecticidal activity, can be applied to the environment of the target pest to control for the pest.

Where the *B.t.* toxin gene is introduced via a suitable DNA construct, e.g., a vector, into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type indigenous microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms such as bacteria, e.g. genera *Pseudomonas, Erwinia, Serratia, Klebsiella, Xanthomonas, Streptomyces, Rhizobium, Sinorhizobium, Rhodopseudomonas, Methylophilius, Agrobacterium, Acetobacter, Lactobacillus, Arthrobacter, Azotobacter, Leuconostoc,* and *Alcaligenes*. Of particular interest are such phytosphere bacterial species as *Pseudomonas syringae, Pseudomonas fluorescens, Serratia marcescens, Acetobacter xylinum, Agrobacterium tumefaciens, Agrobacterium radiobacter, Rhodopseudomonas spheroides, Xanthomonas campestris, Sinorhizobium meliloti* (formerly *Rhizobium meliloti*), *Alcaligenes eutrophus*, and *Azotobacter vinelandii*. Of further interest are fungi, particularly yeast, e.g. genera *Saccharomyces, Cryptococcus, Kluyveromyces, Sporobolomyces, Rhodotorula*, and *Aureobasidium*, and of particular interest are phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms. One highly preferred host is *Pseudomonas fluorescens*.

Isolated Toxin Polypeptides and Compositions of the Invention:

The DIG-303 insecticidal toxin polypeptides of the invention can be treated or prepared, for example, to make a formulated pesticide composition. Examples of formulated pesticide compositions include protein composition, sprayable protein composition, a bait matrix, or in other delivery systems. In one example, B.t. cells or recombinant host cells expressing a DIG-303 insecticidal toxin of the invention can be cultured using standard art media and fermentation techniques. Upon completion of the fermentation cycle, the B.t. spores or other recombinant host cells and/or toxin crystals from the fermentation broth can be isolated by methods known in the art. B.t. spores or recombinant host cells also can be treated prior to being applied or formulated for application to plants. For example, isolated B.t. spores and/or toxin crystals can be chemically treated to prolong insecticidal activity and thereby include a treated polypeptide of the invention. Methods of growing B.t. toxin polypeptides in recombinant hosts and then treating the B.t. to prolong pesticidal activity are known and have been published. See, e.g., U.S. Pat. Nos. 4,695,462, and 4,695,455.

The isolated or treated DIG-303 insecticidal toxin of the invention can be formulated into compositions of finely-divided particulate solids granules, pellets, wettable powders, dusts, aqueous suspensions or dispersions, emulsions, spray, liquid concentrate, or other insecticide formulations. These insecticide formulations are made by combining a DIG-303 insecticide polypeptide herein with adjuvants, diluents, surfactants, dispersants, inert carriers and other components to facilitate handling and application to control one or more target pests. Such formulation ingredients are known in the art, as are methods of application and methods of determining levels of the B.t. spores and/or isolated DIG-303 polypeptide crystals that provide desired insecticidal activity.

Methods for Controlling Insect Pests:

When an insect comes into contact with an effective amount of DIG-303 toxin disclosed herein, which is delivered via an insecticide composition (e.g., a formulated protein composition(s), sprayable protein composition(s), a bait matrix, transgenic plant expression, or another delivery system, the results are typically death of the insect, or the insects do not feed upon the source which makes the toxins available to the insects.

The subject protein toxins can be "applied" or provided to contact the target insects in a variety of ways. For example, the DIG-303 insecticidal toxin of the invention can be applied after being formulated with adjuvants, diluents, carriers, etc. to provide compositions in the form of finely-divided particulate solids, granules, pellets, wettable powders, dusts, aqueous suspensions or dispersions, and emulsions. Alternatively, the DIG-303 insecticidal polypeptide can be delivered by transgenic plants (wherein the protein is produced by and present in the plant) can be used and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject proteins can be appropriately formulated for the desired end use, and then sprayed (or otherwise applied) onto the plant and/or around the plant/to the vicinity of the plant to be protected—before an infestation is discovered, after target insects are discovered, both before and after, and the like. Bait granules, for example, can also be used and are known in the art.

Transgenic Plants.

The DIG-303 insecticidal toxin disclosed herein can be used to protect practically any type of plant from damage by an insect pest. Examples of such plants include potato, eggplant, tomato, pepper, tobacco, and other plants in the nightshade family. Other examples of such plants include maize, sunflower, soybean, cotton, canola, rice, sorghum, wheat, barley, vegetables, ornamentals, peppers (including hot peppers), sugar beets, fruit, and turf, to name but a few. Methods for transforming plants are well known in the art, and illustrative transformation methods are described in the Examples.

A preferred embodiment of the subject invention is the transformation of plants with genes encoding the DIG-303 insecticidal toxin, insecticidal protein, or its variants. The transformed plants are resistant to attack by an insect target pest by virtue of the presence of controlling amounts of the subject insecticidal protein or its variants in the cells of the transformed plant. By incorporating genetic material that encodes the insecticidal properties of the B.t. insecticidal toxins into the genome of a plant eaten by a particular insect pest, the adult or larvae would die after consuming the food plant. Numerous members of the monocotyledonous and dicotyledonous classifications have been transformed. Transgenic agronomic crops as well as fruits and vegetables are of commercial interest. Such crops include but are not limited to maize, rice, soybeans, canola, sunflower, alfalfa, sorghum, wheat, cotton, peanuts, tomatoes, potatoes, and the like. Several techniques exist for introducing foreign genetic material into plant cells, and for obtaining plants that stably maintain and express the introduced gene. Such techniques include acceleration of genetic material coated onto microparticles directly into cells (U.S. Pat. Nos. 4,945,050 and 5,141,131). Plants may be transformed using Agrobacterium technology, see U.S. Pat. No. 5,177,010, European Patent No. EP131624B1, European Patent No. EP159418B1, European Patent No. EP176112B1, U.S. Pat. No. 5,149,645, EP120516B1, U.S. Pat. Nos. 5,464,763, 4,693,976, European Patent No. EP116718B1, European Patent No. EP290799B1, European Patent No. EP320500B1, European Patent No. EP604662B1, U.S. Pat. Nos. 7,060,876, 6,037,526, 6,376,234, European Patent No. EP292435B1, U.S. Pat. Nos. 5,231,019, 5,463,174, 4,762,785, 5,608,142, and 5,159,135. Other transformation technology includes WHISKERS™ technology, see U.S. Pat. Nos. 5,302,523 and 5,464,765. Electroporation technology has also been used to transform plants, see WO1987006614, U.S. Pat. Nos. 5,472,869, 5,384,253, WO199209696, U.S. Pat. No. 6,074,877, WO1993021335, and U.S. Pat. No. 5,679,558. In addition to numerous technologies for trans-forming plants, the type of tissue which is contacted with the foreign genes may vary as well. Such tissue would include but would not be limited to embryogenic tissue, callus tissue type I and type II, hypocotyl, meristem, and the like. Almost all plant tissues may be transformed during dedifferentiation using appropriate techniques within the skill of an artisan.

Genes encoding DIG-303 insecticidal toxins can be inserted into plant cells using a variety of techniques which are well known in the art as disclosed above. For example, a large number of cloning vectors comprising a marker that permits selection of the transformed microbial cells and a replication system functional in *Escherichia coli* are available for preparation and modification of foreign genes for insertion into higher plants. Such manipulations may include, for example, the insertion of mutations, truncations, additions, or substitutions as desired for the intended use. The vectors comprise, for example, pBR322, pUC series, M13mp series, pACYC184, etc. Accordingly, the sequence encoding the Cry protein or variants can be inserted into the vector at a suitable restriction site. The resulting plasmid is used for transformation of *E. coli*, the cells of which are cultivated in a suitable nutrient medium, then harvested and lysed so that workable quantities of the plasmid are recovered. Sequence analysis, restriction fragment analysis, electrophoresis, and other biochemical-molecular biological methods are generally carried out as methods of analysis. After each manipulation, the DNA sequence used can be cleaved and joined to the next DNA sequence. Each manipulated DNA sequence can be cloned in the same or other plasmids.

The use of T-DNA-containing vectors for the transformation of plant cells has been intensively researched and sufficiently described in European Patent No. EP120516B1; Lee and Gelvin (2008), Fraley et al. (1986), and An et al. (1985), and is well established in the field.

Once the inserted DNA has been integrated into the plant genome, it is relatively stable throughout subsequent generations. The vector used to transform the plant cell normally contains a selectable marker gene encoding a protein that confers on the transformed plant cells resistance to a herbicide or an antibiotic, such as phosphinothricin Bialaphos, Kanamycin, Neomycin, G418, Bleomycin, Hygromycin, or a gene which codes for resistance or tolerance to glyphosate, methotrexate, imidazolinones, sulfonylureas and triazolopyrimidine herbicides, such as chlorosulfuron, bromoxynil, dalapon and the like. Of further interest are genes conferring tolerance to herbicides such as haloxyfop, quizalofop, diclofop, and the like, as exemplified by AAD genes (US Patent Application No. 20090093366). The individually employed selectable marker gene should accordingly permit the selection of transformed cells while the growth of cells that do not contain the inserted DNA is suppressed by the selective compound.

A large number of techniques are available for inserting DNA into a host plant cell. Those techniques include transformation with T-DNA delivered by *Agrobacterium tumefaciens* or *Agrobacterium rhizogenes* as the transformation agent. Additionally, fusion of plant protoplasts with liposomes containing the DNA to be delivered, direct injection of the DNA, biolistics transformation (microparticle bombardment), or electroporation, as well as other possible methods, may be employed.

In a preferred embodiment of the subject invention, plants will be transformed with genes wherein the codon usage of the protein coding region has been optimized for plants. See, for example, U.S. Pat. No. 5,380,831. For example, the DIG-303 insecticidal toxin of the invention can be optimized for expression in a dicot such as potato, eggplant, tomato, pepper, tobacco, and another plant in the nightshade family. The DIG-303 insecticidal toxin of the invention can also be optimized for expression in other dicots, or in monocots such as *Zea mays* (corn). Also, advantageously, plants encoding a truncated toxin will be used. The truncated toxin typically will encode about 55% to about 80% of the full length toxin. Methods for creating synthetic *B.t.* genes for use in plants are known in the art (Stewart 2007).

Regardless of transformation technique, the gene is preferably incorporated into a gene transfer vector adapted to express the *B.t.* insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus (CaMV), and the like may be used. Plant-derived promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g. actin, ubiquitin, CaMV 35S). Tissue specific promoters are responsible for gene expression in specific cell or tissue types, such as the leaves or seeds (e.g. zein, oleosin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g. heat shock genes); light (e.g. RUBP carboxylase); hormone (e.g. glucocorticoid); antibiotic (e.g. tetracycline); metabolites; and stress (e.g. drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

The subject invention includes plant cells that are not totipotent (non-totipotent), plant cells that are not propagative material (for example, leaf cells in some embodiments; seed cells are excluded from some embodiments) and are incapable of differentiating into whole plants. The subject invention includes plant cells that have uses other than for regenerating into a whole plant. For example, said plant cell scan be used to produce a protein (such as a DIG-303 protein of the subject invention). Thus, plant cells of the subject invention include those that have uses other than totipotency (that is, some cells of subject invention are not regenerable into a whole plant). However, some embodiments do include seed cells and plant cells that can be regenerated into a whole plant.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by multiple seed companies. These include combinations of IR traits conferred by *B.t.* insecticidal proteins and HT traits such as tolerance to Acetolactate Synthase (ALS) inhibitors such as sulfonylureas, imidazolinones, triazolopyrimidine, sulfonanilides, and the like, Glutamine Synthetase (GS) inhibitors such as Bialaphos, glufosinate, and the like, 4-HydroxyPhenylPyruvate Dioxygenase (HPPD) inhibitors such as mesotrione, isoxaflutole, and the like, 5-EnolPyruvylShikimate-3-Phosphate Synthase (EPSPS) inhibitors such as glyphosate and the like, and Acetyl-Coenzyme A Carboxylase (ACCase) inhibitors such as haloxyfop, quizalofop, diclofop, and the like. Other examples are known in which transgenically provided proteins provide plant tolerance to herbicide chemical classes such as phenoxy acids herbicides and pyridyloxyacetates auxin herbicides (see WO2007053482), or phenoxy acids herbicides and aryloxyphenoxypropionates herbicides (see US Patent Application No. 20090093366). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a *B.t.* insecticidal protein such as that of the subject invention with one or more additional HT traits such as those mentioned above, plus one or more additional input traits (e.g., other insect resistance conferred by *B.t.*-derived or other insecticidal proteins, insect resistance conferred by mechanisms such as RNAi and the like, nematode resistance, disease resistance, stress tolerance, improved nitrogen utilization, and the like), or output traits (e.g., high oils content, healthy oil composition, nutritional improvement, and the like). Such combinations may be obtained either through conventional breeding (breeding stack) or jointly as a novel transformation event involving the simultaneous introduction of multiple genes (molecular stack or co-transformation). Benefits include the ability to manage insect pests and improved weed control in a crop plant that provides secondary benefits to the producer and/or the consumer. Thus, the subject invention can be used in combination with other traits to provide a complete agronomic package of improved crop quality with the ability to flexibly and cost effectively control any number of agronomic issues.

Target Pests. The DIG-303 insecticidal toxins of the invention are particularly suitable for use in control of insects pests. Coleopterans are one important group of agricultural, horticultural, and household pests which cause a very large amount of damage each year. This large insect order encompasses foliar- and root-feeding larvae and adults, including members of, for example, the insect families-Chrysomelidae, Coccinellidae, Curculionidae, Dermestidae, Elateridae, Scarabaeidae, Scolytidae, and Tenebrionidae. Included within these families are leaf beetles and leaf miners in the family Chrysomelidae, potato beetles (e.g., Colorado Potato Beetle (*Leptinotarsa decemlineata* Say), grape *colaspis* (*Colaspis brunnea* Fabricius), cereal leaf beetle (*Oulema melanopus* Linnaeus), sunflower beetle (*Zygogramma exclamationis* Fabricius)), and beetles in the family Coccinellidae (e.g., Mexican bean beetle (*Epilachna varivestis* Mulsant)). Further examples are chafers and other beetles in the family Scarabaeidae (e.g., Japanese beetle (*Popillia japonica* Newman), northern masked chafer (white grub, *Cyclocephala borealis* Arrow), southern masked chafer (white grub, *Cyclocephala* immaculata Olivier), European chafer (*Rhizotrogus majalis* Razoumowsky), white grub (*Phyllophaga crinita* Burmeister), carrot beetle (*Ligyrus gibbosus* De Geer), and chafers of the genera *Holotrichia* spp and *Melolontha* spp.). Further examples of coleopteran insects are weevils (e.g., boll weevil (*Anthonomus grandis* Boheman), rice water weevil (*Lissorhoptrus oryzophilus* Kuschel), granary weevil (*Sitophilus grananus* Linnaeus), rice weevil (*Sitophilus oryzae* Linnaeus), and clover leaf weevil (*Hypera punctata* Fabricius)). Also included are maize billbug (*Sphenophorus maidis* Chittenden), flea beetles (e.g., corn flea beetle (*Chaetocnema pulicara* Melsheimer), and crucifer flea beetle (*Phyllotreta cruciferae* Goeze)), spotted cucumber beetle (*Diabrotica undecimpunctata*), and rootworms, (e.g., western corn rootworm (*Diabrotica virgifera virgifera* LeConte), northern corn rootworm (*Diabrotica barben* Smith & Lawrence), and southern corn rootworm (*Diabrotica undecimpunctata howardi* Barber)). Further examples of coleopteran pests are beetles of the family Rutelinae (shining leaf chafers) such as the genus *Anomala* (including *A. marginata, A. lucicola, A. oblivia* and *A. orientalis*). Additional coleopteran insects are carpet beetles from the family Dermestidae, wireworms from the family Elateridae (e.g., *Melanotus* spp., *Conoderus* spp., *Limonius* spp., *Agriotes* spp., *Ctenicera* spp., *Aeolus* spp.)), bark beetles from the family Scolytidae, and beetles from the family Tenebrionidae (e.g. *Eleodes* spp). Any genus listed above (and others), generally, can also be targeted as a part of the subject invention by insecticidal compositions including DIG-303 insecticidal polypeptide alone or in combination with another insecticidal agent. Any additional insects in any of these genera (as targets) are also included within the scope of this invention.

Use of DIG-303 insecticidal toxins to control coleopteran pests of crop plants is contemplated. In some embodiments, Cry proteins may be economically deployed for control of insect pests that include but are not limited to, for example, rootworms such as western corn rootworm (*Diabrotica virgifera virgifera* LeConte), northern corn rootworm (*Diabrotica barberi* Smith & Lawrence), and southern corn rootworm (*Diabrotica undecimpunctata howardi* Barber), and grubs such as the larvae of *Cyclocephala borealis* (northern masked chafer), *Cyclocephala immaculate* (southern masked chafer), and *Popillia japonica* (Japanese beetle).

Lepidopterans are another important group of agricultural, horticultural, and household pests which cause a very large amount of damage each year. The invention provides use of DIG-303 toxins in combination with other insecticides to control insect pests within this order is within the scope of this invention. This insect order encompasses foliar- and root-feeding larvae and adults, including members of, for example, the insect families Arctiidae, Gelechiidae, Geometridae, Lasiocampidae, Lymantriidae, Noctuidae, Pyralidae, Sesiidae, Sphingidae, Tineidae, and Tortricidae. Lepidopteran insect pests include, but are not limited to: *Achoroia grisella, Acleris gloverana, Acleris variana, Adoxophyes orana, Agrotis ipsilon* (black cutworm), *Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmia feneralis, Diaphania hyalinata, Diaphania nitidalis, Diatraea grandiosella* (southwestern corn borer), *Diatraea saccharalis* (sugarcane borer), *Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea* (corn earworm), *Heliothis virescens* (tobacco budworm), *Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxagrotis albicosta* (western bean cutworm), *Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra pieta, Operophtera brumata, Orgyia* sp., *Ostrinia nubilalis* (European corn borer), *Paleacrita vernata, Papiapema nebris* (common stalk borer), *Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella* (diamondback moth), *Pontia protodice,*

*Pseudaletia unipuncta* (armyworm), *Pseudoplasia includens, Sabulodes aegrotata, Schizura concinna, Sitotroga cerealella, Spilonta ocellana, Spodoptera frugiperda* (fall armyworm), *Spodoptera exigua* (beet armyworm), *Thaurnstopoea pityocampa, Ensola bisselliella, Trichoplusia ni*, (cabbage looper), *Udea rubigalis, Xylomyges curiails,* and *Yponomeuta padella.*

Use of the DIG-303 insecticidal toxins to control parasitic nematodes including, but not limited to, root knot nematode (*Meloidogyne incognita*) and soybean cyst nematode (*Heterodera glycines*) is also contemplated.

Anti-Toxin Antibodies:

Antibodies to the toxins disclosed herein, or to equivalent toxins, or fragments of these toxins, can readily be prepared using standard procedures in this art. Such antibodies are useful to detect the presence of the DIG-303 toxins.

Once the *B.t.* insecticidal toxin has been isolated, antibodies specific for the toxin may be raised by conventional methods that are well known in the art. Repeated injections into a host of choice over a period of weeks or months will elicit an immune response and result in significant anti-*B.t.* toxin serum titers. Preferred hosts are mammalian species and more highly preferred species are rabbits, goats, sheep and mice. Blood drawn from such immunized animals may be processed by established methods to obtain antiserum (polyclonal antibodies) reactive with the *B.t.* insecticidal toxin. The antiserum may then be affinity purified by adsorption to the toxin according to techniques known in the art. Affinity purified antiserum may be further purified by isolating the immunoglobulin fraction within the antiserum using procedures known in the art. The resulting material will be a heterogeneous population of immunoglobulins reactive with the *B.t.* insecticidal toxin.

Anti-*B.t.* toxin antibodies may also be generated by preparing a semi-synthetic immunogen consisting of a synthetic peptide fragment of the *B.t.* insecticidal toxin conjugated to an immunogenic carrier. Numerous schemes and instruments useful for making peptide fragments are well known in the art. Many suitable immunogenic carriers such as bovine serum albumin or keyhole limpet hemocyanin are also well known in the art, as are techniques for coupling the immunogen and carrier proteins. Once the semi-synthetic immunogen has been constructed, the procedure for making antibodies specific for the *B.t.* insecticidal toxin fragment is identical to those used for making antibodies reactive with natural *B.t.* toxin.

Anti-*B.t.* toxin monoclonal antibodies (MAbs) are readily prepared using purified *B.t.* insecticidal toxin. Methods for producing MAbs have been practiced for over 20 years and are well known to those of ordinary skill in the art. Repeated intraperitoneal or subcutaneous injections of purified *B.t.* insecticidal toxin in adjuvant will elicit an immune response in most animals. Hyperimmunized B-lymphocytes are removed from the animal and fused with a suitable fusion partner cell line capable of being cultured indefinitely. Preferred animals whose B-lymphocytes may be hyperimmunized and used in the production of MAbs are mammals. More preferred animals are rats and mice and most preferred is the BALB/c mouse strain.

Numerous mammalian cell lines are suitable fusion partners for the production of hybridomas. Many such lines are available from the American Type Culture Collection (ATCC, Manassas, Va.) and commercial suppliers. Preferred fusion partner cell lines are derived from mouse myelomas and the HL-1® Friendly myeloma-653 cell line (Ventrex, Portland, Me.) is most preferred. Once fused, the resulting hybridomas are cultured in a selective growth medium for one to two weeks. Two well known selection systems are available for eliminating unfused myeloma cells, or fusions between myeloma cells, from the mixed hybridoma culture. The choice of selection system depends on the strain of mouse immunized and myeloma fusion partner used. The AAT selection system, described by Taggart and Samloff (1983), may be used; however, the HAT (hypoxanthine, aminopterin, thymidine) selection system, described by Littlefield (1964), is preferred because of its compatibility with the preferred mouse strain and fusion partner mentioned above. Spent growth medium is then screened for immunospecific MAb secretion. Enzyme linked immunosorbent assay (ELISA) procedures are best suited for this purpose; though, radioimmunoassays adapted for large volume screening are also acceptable. Multiple screens designed to consecutively pare down the considerable number of irrelevant or less desired cultures may be performed. Cultures that secrete MAbs reactive with the *B.t.* insecticidal toxin may be screened for cross-reactivity with known *B.t.* insecticidal toxins. MAbs that preferentially bind to the preferred *B.t.* insecticidal toxin may be isotyped using commercially available assays. Preferred MAbs are of the IgG class, and more highly preferred MAbs are of the $IgG_1$ and $IgG_{2a}$ subisotypes.

Hybridoma cultures that secrete the preferred MAbs may be sub-cloned several times to establish monoclonality and stability. Well known methods for sub-cloning eukaryotic, non-adherent cell cultures include limiting dilution, soft agarose and fluorescence activated cell sorting techniques. After each subcloning, the resultant cultures preferably are re-assayed for antibody secretion and isotype to ensure that a stable preferred MAb-secreting culture has been established.

The anti-*B.t.* toxin antibodies are useful in various methods of detecting the claimed *B.t.* insecticidal toxin of the instant invention, and variants or fragments thereof. It is well known that antibodies labeled with a reporting group can be used to identify the presence of antigens in a variety of milieus. Antibodies labeled with radioisotopes have been used for decades in radioimmunoassays to identify, with great precision and sensitivity, the presence of antigens in a variety of biological fluids. More recently, enzyme labeled antibodies have been used as a substitute for radiolabeled antibodies in the ELISA assay. Further, antibodies immunoreactive to the *B.t.* insecticidal toxin of the present invention can be bound to an immobilizing substance such as a polystyrene well or particle and used in immunoassays to determine whether the *B.t.* toxin is present in a test sample.

Detection Using Probes:

A further method for identifying the toxins and genes of the subject invention is through the use of oligonucleotide probes. These probes are detectable nucleotide sequences. These sequences may be rendered detectable by virtue of an appropriate radioactive label or may be made inherently fluorescent as described in U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization:

As is well known to those skilled in molecular biology, similarity of two nucleic acids can be characterized by their tendency to hybridize. As used herein the terms "stringent conditions" or "stringent hybridization conditions" are intended to refer to conditions under which a probe will hybridize (anneal) to its target sequence to a detectably greater degree than to other sequences (e.g. at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA/DNA hybrids, the thermal melting point ($T_m$) is the temperature (under defined ionic strength and pH) at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the $T_m$ can be approximated from the equation of Meinkoth and Wahl (1984):

$$T_m(° C.)=81.5° C.+16.6(\log M)+0.41 (\% GC)-0.61 (\% \text{formamide})-500/L;$$

where M is the molarity of monovalent cations, % GC is the percentage of guanosine and cytosine nucleotides in the DNA, % formamide is the percentage of formamide in the hybridization solution (w/v), and L is the length of the hybrid in base pairs.

Alternatively, the $T_m$ is described by the following formula (Beltz et al., 1983). $T_m(° C.)=81.5° C.+16.6(\log [Na+])+0.41 (\% GC)-0.61 (\% \text{formamide})-600/L$ where [Na+] is the molarity of sodium ions, % GC is the percentage of guanosine and cytosine nucleotides in the DNA, % formamide is the percentage of formamide in the hybridization solution (w:v), and L is the length of the hybrid in base pairs Using the equations, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) and Ausubel et al. (1995). Also see Sambrook et al. (1989).

Hybridization of immobilized DNA on Southern blots with radioactively labeled gene-specific probes may be performed by standard methods (Sambrook et al., supra.). Radioactive isotopes used for labeling polynucleotide probes may include 32P, 33P, 14C, or 3H. Incorporation of radioactive isotopes into polynucleotide probe molecules may be done by any of several methods well known to those skilled in the field of molecular biology. (See, e.g. Sambrook et al., supra.) In general, hybridization and subsequent washes may be carried out under stringent conditions that allow for detection of target sequences with homology to the claimed toxin encoding genes. For double-stranded DNA gene probes, hybridization may be carried out overnight at 20° C. to 25° C. below the $T_m$ of the DNA hybrid in 6×SSPE, 5×Denhardt's Solution, 0.1% SDS, 0.1 mg/mL denatured DNA (20×SSPE is 3M NaCl, 0.2 M NaHPO$_4$, and 0.02M EDTA (ethylenediamine tetra-acetic acid sodium salt); 100× Denhardt's Solution is 20 gm/L Polyvinylpyrollidone, 20 gm/L Ficoll type 400 and 20 gm/L Bovine Serum Albumin (fraction V)).

Washes may typically be carried out as follows:

Twice at room temperature for 15 minutes in 1×SSPE, 0.1% SDS (low stringency wash).

Once at $T_m$-20° C. for 15 minutes in 0.2×SSPE, 0.1% SDS (moderate stringency wash).

For oligonucleotide probes, hybridization may be carried out overnight at 10° C. to 20° C. below the $T_m$ of the hybrid in 6×SSPE, 5×Denhardt's solution, 0.1% SDS, 0.1 mg/mL denatured DNA. $T_m$ for oligonucleotide probes may be determined by the following formula (Suggs et al., 1981).

$$T_m(° C.)=2 \text{ (number of } T/A \text{ base pairs)}+4 \text{ (number of } G/C \text{ base pairs)}$$

Washes may typically be carried out as follows:

Twice at room temperature for 15 minutes 1×SSPE, 0.1% SDS (low stringency wash).

Once at the hybridization temperature for 15 minutes in 1×SSPE, 0.1% SDS (moderate stringency wash).

Probe molecules for hybridization and hybrid molecules formed between probe and target molecules may be rendered detectable by means other than radioactive labeling. Such alternate methods are intended to be within the scope of this invention.

All patents, patent applications, provisional applications, and publications referred to or cited herein are incorporated by reference in their entirety to the extent they are not inconsistent with the explicit teachings of this specification.

By the use of the term "genetic material" herein, it is meant to include all genes, nucleic acid, DNA and RNA. The term "dsRNA" refers to double-stranded RNA. For designations of nucleotide residues of polynucleotides, DNA, RNA, oligonucleotides, and primers, and for designations of amino acid residues of proteins, standard IUPAC abbreviations are employed throughout this document. Nucleic acid sequences are presented in the standard 5' to 3' direction, and protein sequences are presented in the standard amino (N) terminal to carboxy (C) terminal direction.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

Unless specifically indicated or implied, the terms "a", "an", and "the" signify "at least one" as used herein.

All percentages are by weight and all solvent mixture proportions are by volume unless otherwise noted. All temperatures are in degrees Celsius.

Example 1

Isolation of a Gene Encoding DIG-303 Toxin

Unless otherwise indicated, molecular biological and biochemical manipulations described in this and subsequent Examples were performed by standard methodologies as disclosed in, for example, Ausubel et al. (1995), and Sambrook et al. (1989), and updates thereof. A nucleic acid encoding the insecticidal Cry protein designated herein as DIG-303 was isolated from *B.t.* strain PS18A also known as DBt10340. Degenerate Forward and Reverse primers for Polymerase Chain Reactions (PCR) were designed and used to amplify a DNA fragment with homology to Cry32 from a genomic DNA library. The determined sequence of the amplified fragment was used for additional genome walking to obtain the complete open reading frame of DIG-303. SEQ ID NO:1 is the 3771 bp nucleotide sequence encoding the full length DIG-303 protein. SEQ ID NO:2 is the 1257 amino acid sequence of the full length DIG-303 protein deduced from SEQ ID NO:1.

Example 2

DIG-303 Chimeric Toxin in Bacterial Hosts

Standard cloning methods were used in the construction of *Pseudomonas fluorescens* (*Pf*) expression plasmids engineered to produce DIG-303 chimera toxin consisting of the DIG-303 core toxin encoding sequence (encoding amino acids 1-685) and the Cry1Ab C-terminal protoxin encoding segment as described above, each encoded by the maize-optimized coding sequences. Restriction endonucleases were obtained from New England BioLabs (NEB; Ipswich, Mass.) and T4 DNA Ligase (Invitrogen) were used for DNA ligation. Plasmid preparations were performed using the NucleoSpin® Plasmid Kit (Macherey-Nagel Inc, Bethlehem, Pa.) following the instructions of the supplier. DNA fragments were purified using the QIAquick Gel Extraction kit (Qiagen) after agarose Tris-acetate gel electrophoresis. The linearized vector was phosphatased with NEB Antarctic Phosphatase to enhance formation of recombinant molecules.

The basic cloning strategy entailed subcloning a DNA fragment having the DIG-303 Cry1Ab chimera coding sequence (CDS) into pDOW1169 at, for example, SpeI and SalI restriction sites, whereby the DIG-303 chimera CDS was placed under the expression control of the Ptac promoter and the rrnBT1T2 terminator from plasmid pKK223-3 (PL Pharmacia, Milwaukee, Wis.). pDOW1169 was a medium copy plasmid with the RSF1010 origin of replication, a pyrF gene, and a ribosome binding site preceding the restriction enzyme recognition sites into which DNA fragments containing protein coding regions are introduced (U.S. Pat. No. 7,618,799). The expression plasmids were transformed by electroporation into DC454 (a near wild-type *P. fluorescens* strain having mutations ΔpyrF and lsc::lacIQI), or its derivatives, recovered in SOC-Soy hydrolysate medium, and plated on selective medium (M9 glucose agar lacking uracil, Sambrook et al., supra). Details of the transformation and selection methods are generally described available in Squires et al. (2004), US Patent Application No. 20060008877, U.S. Pat. No. 7,681,799, and US Patent Application No. 20080058262, incorporated herein by reference. Recombinant colonies were identified by restriction digestion of miniprep plasmid DNA. Various culture media suitable for growth of *Pseudomonas fluorescens* may be utilized, for example, as described in Huang et al. 2007 and US Patent Application No. 20060008877 in cells from *P. fluorescens* fermentations that produced insoluble *B.t.* insecticidal protein inclusion bodies.

Production of DIG-303 chimera for characterization and insect bioassay was accomplished by shake-flask-grown *P. fluorescens* strains harboring expression constructs. Seed cultures grown in M9 medium supplemented with glucose and trace elements were used to inoculate defined minimal medium. Expression of the DIG-303 chimera coding sequences were induced by addition of isopropyl-β-D-1-thiogalactopyranoside (IPTG) after an initial incubation of 24 hours at 30° C. with shaking. Cultures were sampled at the time of induction and at various times post-induction. Cell density was measured by optical density at 600 nm ($OD_{600}$). Other culture media suitable for growth of *Pseudomonas fluorescens* may also be utilized, for example, as described in Huang et al. 2007 and US Patent Application No. 20060008877 in cells from *P. fluorescens* fermentations that produced insoluble *B.t.* insecticidal protein inclusion bodies (IB). Briefly, cells were lysed, pellet and supernatant fractions were prepared by centrifugation, the pellet was resuspended and repeatedly washed by resuspension in lysis buffer until the supernatant became colorless and the IB pellet became firm and off-white in color. The final pellet was washed, resuspended in sterile-filtered distilled water containing 2 mM EDTA, and stored at −80° C. The supernatant fraction was enriched for the recombinant protein by column chromatography.

Preparations were analyzed by SDS_PAGE. Quantification of target bands was done by comparing densitometric values for the bands against Bovine Serum Albumin (BSA) samples run on the same gel to generate a standard curve. The sample buffer was then changed to 10 mM CAPS (3-(cyclohexamino)1-propanesulfonic acid) pH10, using disposable PD-10 columns (GE Healthcare, Piscataway, N.J.).

The concentrated extract was analyzed and quantified by SDS_PAGE relative to background-subtracted BSA standards to generate a standard curve to calculate the concentration of DIG-303 chimera.

Example 3

Design of a Maize Codon-Optimized Sequence SEQ ID NO:3

One skilled in the art of plant molecular biology will understand that multiple DNA sequences may be designed to encode a single amino acid sequence. A common means of increasing the expression of a coding region for a protein of interest is to tailor the coding region in such a manner that its codon composition resembles the overall codon composition of the host in which the gene is destined to be expressed. Guidance regarding the design and production of synthetic genes can be found in, for example, WO1997013402, U.S. Pat. Nos. 6,166,302, and 5,380,831.

A DNA sequence having a maize codon bias was designed and synthesized to produce a DIG-303 insecticidal protein in transgenic monocot plants. A codon usage table for maize (Zea mays L.) was calculated from hundreds of protein coding sequences obtained from sequences deposited in GenBank (www.ncbi.nlm.nih.gov). A resealed maize codon set was calculated after omitting any synonymous codon used less than about 10% of total codon uses for that amino acid.

To derive the maize-codon-optimized DNA sequence encoding the DIG-303 protein of SEQ ID NO:3, or insecticidal fragments thereof, substitutions to the native DIG-303 DNA sequence (SEQ ID NO:1) were made such that the resulting DNA sequence had the overall codon composition of the maize-optimized codon bias table. Further refinements of the sequences were made to eliminate undesirable restriction enzyme recognition sites, potential plant intron splice sites, long runs of A/T or C/G residues, and other motifs that might interfere with mRNA stability, transcription, or translation of the coding region in plant cells. Other changes were made to introduce desired restriction enzyme recognition sites, and to eliminate long internal Open Reading Frames (frames other than +1). These changes were all made within the constraints of retaining the maize-biased Resealed codon composition.

Example 4

Construction of an Expression Plasmid Encoding the DIG-303 Toxin in Bacterial Hosts Standard cloning methods were used in the construction of Pseudomonas fluorescens (Pf) expression plasmids engineered to produce DIG-303 encoded by the maize-optimized coding sequences. Restriction endonucleases were obtained from New England BioLabs (NEB; Ipswich, Mass.) and T4 DNA Ligase (Invitrogen) was used for DNA ligation. Plasmid preparations were performed using the NucleoSpin® Plasmid Kit (Macherey-Nagel Inc, Bethlehem, Pa.) following the instructions of the supplier. DNA fragments were purified using the QIAquick Gel Extraction kit (Qiagen) after agarose Tris-acetate gel electrophoresis. The linearized vector was phosphatased with NEB Antarctic Phosphatase to enhance formation of recombinant molecules.

A DNA fragment having the DIG-303 coding sequence (CDS), as provided by SEQ ID NO:3, was subcloned into pDOW1169 at, for example, SpeI and SalI restriction sites, whereby the DIG-303 CDS was placed under the expression control of the Ptac promoter and the rrnBT1T2 terminator from plasmid pKK223-3 (PL Pharmacia, Milwaukee, Wis.). pDOW1169 is a medium copy plasmid with the RSF1010 origin of replication, a pyrF gene, and a ribosome binding site preceding the restriction enzyme recognition sites into which DNA fragments containing protein coding regions may be introduced (U.S. Pat. No. 7,618,799). The expression plasmid (pDAB107162, containing the DIG-303 coding sequence) was transformed by electroporation into DC454 (a near wild-type P. fluorescens strain having mutations ΔpyrF and lsc::lacIQI), or derivatives thereof, recovered in SOC-Soy hydrolysate medium, and plated on selective medium (M9 glucose agar lacking uracil, Sambrook et al., supra). The transformation and selection methods are generally described available in Squires et al. (2004), US Patent Application No. 20060008877, U.S. Pat. No. 7,681,799, and US Patent Application No. 20080058262, incorporated herein by reference. Recombinant colonies were identified by restriction digestion of miniprep plasmid DNA. The resulting expression strain is known as DPf21990 in the Dow AgroSciences Recombinant Culture Collection.

Example 5

Preparation of DIG-303 Protein Samples

Production of DIG-303 for characterization and insect bioassay was accomplished by expression of DIG-303 in shake-flask-grown P. fluorescens strain DPf21990 which harbors expression plasmid pDAB107162. Seed cultures grown in M9 medium supplemented with glucose and trace elements were used to inoculate defined minimal medium. Expression of the DIG-303 coding region was induced by addition of isopropyl-β-D-1-thiogalactopyranoside (IPTG) after an initial incubation of 24 hours at 30° C. with shaking. Cultures were sampled at the time of induction and at various times post-induction. Cell density was measured by optical density at 600 nm ($OD_{600}$). The final pellet was washed, resuspended in sterile-filtered distilled water containing 2 mM EDTA, and stored at −80° C. The inclusion body (IB) pellet was collected by centrifugation, resuspended and repeatedly washed by resuspension in lysis buffer until the supernatant became colorless and the IB pellet became firm and off-white in color.

IB preparations were analyzed by SDS_PAGE. Quantification of target bands was done by comparing densitometric values for the bands against Bovine Serum Albumin (BSA) samples run on the same gel to generate a standard curve. Target protein was subsequently extracted from the inclusion body using 10 mM CAPS (3-(cyclohexamino)1-propanesulfonic acid) buffer, pH10 and gently rocking on a platform at 4° C. overnight. Solubilized DIG-303 was centrifuged and the resulting supernatant was concentrated. The concentrated extract was analyzed and quantified by SDS PAGE relative to background-subtracted BSA standards to generate a standard curve to calculate the concentration of DIG-303.

Example 6

Insect Activity of DIG-303 Insecticidal Toxin

DIG-303 was tested and found to have insecticidal activity on larvae of the coleopteran insect, the Colorado potato beetle (Leptinotarsa decemlineata).

A solution containing whole cells (Table 2) or purified proteins (either solubilized or as inclusion bodies; Table 4) were tested for insecticidal activity in bioassays conducted with second instar Colorado potato beetle (CPB, *Leptinotarsa decimlineata*) larvae. Insect eggs were received from Bayer Corp (Pittsburg, Pa.).

Bioassays were conducted in 128-well plastic trays. Each well contained 0.5 mL of water agar and one 1.5 cm diameter Eggplant (*Solanum melongena*) "Black Beauty" leaf disk cut with a cork borer. Test leaf disks were treated with 40 µl of triple diluted DIG-303 whole cells. Leaf disks used as positive controls for insecticide activity were treated with 1 µg/mL of Cry3Aa full length protoxin. Negative control leaf disks were treated with buffer or were left untreated.

Treated leaf disks were held in a fume hood until the liquid on the surface had evaporated or was absorbed into the diet. Approximately 2 days after eclosion, individual larvae were picked up with a moistened camelhair brush and deposited on a treated leaf disc, one larva per well. The infested wells were then sealed with adhesive sheets of clear plastic that are vented to allow gas exchange (C-D International, Pitman, N.J.). Eleven to sixteen replications were completed for each treatment listed above. After two days incubation, the estimated percentage of leaf disk damage, the number of dead insects, and the weight of surviving insects were recorded. Bioassay trays were held under controlled environmental conditions (28° C., ~40% Relative Humidity, 16:8 (Light:Dark)). Percent mortality and percent growth inhibition were calculated for each treatment. Growth inhibition (GI) is calculated as follows:

$$GI=[1-(TWIT/TNIT)/(TWIBC/TNIBC)]$$

where TWIT is the Total Weight of Insects in the Treatment, TNIT is the Total Number of Insects in the Treatment, TWIBC is the Total Weight of Insects in the Background Check (Buffer control), and TNIBC is the Total Number of Insects in the Background Check (Buffer control). Bioassay results are summarized in Table 2 and Table 4, below. Bioassay results show there was less leaf damage and increased growth inhibition for the whole cell DIG-303 1:10 dilution treatment (Table 2). Replicated bioassays demonstrated that ingestion of DIG-303 preparations caused mortality and growth inhibition of Colorado potato beetle (Table 4).

TABLE 2

Percent mortality, proportion of leaf disk damage, and growth inhibition in whole *Pseudomonas* cell activity bioassay of DIG-303 on Colorado potato beetle after five days.

| Leaf Treatment | Number of Insects Tested | Proportion Leaf Damage | Percent Mortality | GI (%) |
| --- | --- | --- | --- | --- |
| Whole cell DIG-303 1:10 dilution | 11 | 0.03 | 45 | 76 |
| Whole cell DIG-303 1:30 dilution | 16 | 0.74 | 13 | 5 |
| Cry3Aa 1:30 dilution (Positive Control) | 16 | 0.00 | 75 | 92 |
| Buffer 10 mM PBS (Negative Control) | 16 | 1.00 | 19 | 0 |
| Soluble protein Cry1Ac spike 1:30 dilution | 16 | 0.68 | 20 | 21 |
| UNTREATED | 16 | 1.64 | 0 | 0 |

DIG-303 was tested and found to have insecticidal activity on larvae of the lepidopteran insect diamondback moth (*Plutella xylostella*) (Table 3). Diamondback moth (DBM) bioassays were conducted in 96-well bioassay trays (C-D International, Pitman, N.J.). A 20 µl aliquot of triple diluted whole cell suspension was delivered onto the surface of multispecies lepidopteran diet (Southland Products, Lake Village, Ark.) in each well. The treated trays were air dried, and one individual larva (24 to 48 h after eclosion) was deposited on the treated diet surface. The infested wells were then sealed with adhesive sheets of clear plastic, vented to allow gas exchange (C-D International, Pitman, N.J.). Bioassay trays were held under controlled environmental conditions (28° C., 40% relative humidity, 16:8 h light:dark photoperiod) for 5 days. Replicated bioassays demonstrated that ingestion of DIG-303 preparations caused mortality of diamondback moth (Table 3).

DIG-303 was tested and found to have insecticidal activity on larvae of the coleopteran insect corn rootworm (*Diabrotica vigifera vigifera*) (Table 5). For *D. virgifera virgifera*, methods similar to the DBM insect bioassays were followed, except that bioassays were conducted in 128-well bioassay trays and a Dow AgroSciences LLC proprietary rootworm diet was used and 80 to 100 µl of aliquot solution was used to treat the diet surface. The total number of insects exposed to each protein sample, the number of dead insects, and the weight of surviving insects were recorded in all insect bioassays. For the western corn rootworm assay trypsin activated Cry3Aa and Cry34+Cry35 were used as positive controls. Negative controls included water; untreated; Cry1F; 20 mM NaCitrate, p.H. 3.5; and 10 mM CAPS, pH 10.

TABLE 3

Percent mortality of diamondback moth in whole *Pseudomonas* cell activity bioassay of DIG-303 after five days.

| Treatment | Number of Insects Tested | % Mortality |
| --- | --- | --- |
| Whole cell DIG-303 1:10 dilution | 7 | 71.43 |
| Whole cell DIG-303 1:30 dilution | 7 | 71.43 |
| Empty vector (DPf5) 1:10 dilution | 5 | 40 |
| Empty vector (DPf5) 1:30 dilution | 5 | 0 |
| PBS | 8 | 0 |
| Untreated | 32 | 0 |
| Cry1Ac (Positive control) | 2 | 100 |
| Cry3Aa | 2 | 100 |

Enriched DIG-303 from inclusion bodies was tested on the lepidopteran insects, methods similar to the DBM insect bioassays were followed for corn earworm (CEW), European corn borer (ECB), and fall armyworm (FAW) using methods similar to the tests done on diamondback moth. No activity was observed against CEW, ECB, and FAW, (data not shown).

TABLE 4

DIG-303 protein from inclusion bodies solubilized (10 mM CAPS pH 10) and tested against Colorado potato beetle

| Insect | Treatment | Dose (ng/cm2) | N | Average % Mortality | St.Dev. (%) | Average GI | St.Dev. |
| --- | --- | --- | --- | --- | --- | --- | --- |
| CPB | DIG-303 | 9000 | 3 | 77.20 | 34.10 | 0.93 | 0.12 |
| CPB | Untreated | 0 | 3 | 4.30 | 7.50 | 0.047 | 0.06 |
| CPB | Water | 0 | 3 | 0.00 | 0.00 | 0.02 | 0.05 |
| CPB | Cry3Aa (Positive Control) | 1000 | 3 | 92.00 | 14.00 | 1 | 0 |

TABLE 4-continued

DIG-303 protein from inclusion bodies solubilized (10 mM CAPS pH 10) and tested against Colorado potato beetle

| Insect | Treatment | Dose (ng/cm2) | N | Average % Mortality | St.Dev. (%) | Average GI | St.Dev. |
|---|---|---|---|---|---|---|---|
| CPB | Buffer 10 mM CAPS pH 10 (Negative Control) | 0 | 3 | 6.00 | 10.00 | 0 | 0 |
| CPB | BSA | 9000 | 2 | 9.00 | 13.00 | 0.26 | 0.34 |
| CPB | Tryspin treated DIG-303 | 9000 | 1 | 75.00 | NA | 0.98 | NA |

TABLE 5

DIG-303 protein from inclusion bodies solubilized (10 mM CAPS pH 10) and

Example 8

Production of DIG-303 Insecticidal Toxins in Dicot Plants

*Arabidopsis* Transformation

*Arabidopsis thaliana* Col-01 is transformed using the floral dip method (Weigel and Glazebrook, 2002). The selected *Agrobacterium* colony is used to inoculate 1 mL to 15 mL cultures of YEP broth containing appropriate antibiotics for selection. The culture is incubated overnight at 28° C. with constant agitation at 220 rpm. Each culture is used to inoculate two 500 mL cultures of YEP broth containing appropriate antibiotics for selection and the new cultures are incubated overnight at 28° C. with constant agitation. The cells are pelleted at approximately 8700× g for 10 minutes at room temperature, and the resulting supernatant is discarded. The cell pellet is gently resuspended in 500 mL of infiltration media containing ½× Murashige and Skoog salts (Sigma-Aldrich)/Gamborg's B5 vitamins (Gold BioTechnology, St. Louis, Mo.), 10% (w/v) sucrose, 0.044 µM benzylaminopurine (10 µL/liter of 1 mg/mL stock in DMSO) and 300 µL/liter Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22° C., with a 16-hour light/8-hour dark photoperiod. Approximately 4 weeks after dipping, the seeds are harvested.

*Arabidopsis* Growth and Selection

Freshly harvested T1 seed is allowed to dry for at least 7 days at room temperature in the presence of desiccant. Seed is suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution (Hoagland and Arnon, 1950) until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron™ growth chamber (Models CMP4030 or CMP3244; Controlled Environments Limited, Winnipeg, Manitoba, Canada) under long day conditions (16 hours light/8 hours dark) at a light intensity of 120-150 µmol/m²sec under constant temperature (22° C.) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a pat or bar gene (Wehrmann et al., 1996), transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and transplanted into pots prepared with Sunshine Mix LP5. Transplanted plants are covered with a humidity dome for 3-4 days and placed in a Conviron™ growth chamber under the above-mentioned growth conditions.

Those skilled in the art of dicot plant transformation will understand that other methods of selection of transformed plants are available when other plant expressible selectable marker genes (e.g. herbicide tolerance genes) are used.

Insect Bioassays of Transgenic *Arabidopsis*

Transgenic *Arabidopsis* lines expressing DIG-303 insecticidal toxin proteins are demonstrated to be active against sensitive insect species in artificial diet overlay assays. Protein extracted from transgenic and non-transgenic *Arabidopsis* lines is quantified by appropriate methods and sample volumes are adjusted to normalize protein concentration. Bioassays are conducted on artificial diet as described above. Non-transgenic *Arabidopsis* and/or buffer and water are included in assays as background check treatments.

Example 9

*Agrobacterium* Transformation for Generation of Superbinary Vectors

The *Agrobacterium* superbinary system is conveniently used for transformation of monocot plant hosts. Methodologies for constructing and validating superbinary vectors are well established. See, for example, European Patent No. EP604662B1 and U.S. Pat. No. 7,060,876. Standard molecular biological and microbiological methods are used to generate superbinary plasmids. Verification/validation of the structure of the superbinary plasmid is done using methodologies as described above for binary vectors.

Example 10

Production of DIG-303 Insecticidal Toxins in Monocot Plants

*Agrobacterium*-Mediated Transformation of Maize

Seeds from a High II $F_1$ cross (Armstrong et al., 1991) are planted into 5-gallon-pots containing a mixture of 95% Metro-Mix 360 soilless growing medium (Sun Gro Horticulture, Bellevue, Wash.) and 5% clay/loam soil. The plants are grown in a greenhouse using a combination of high pressure sodium and metal halide lamps with a 16:8 hour Light:Dark photoperiod. For obtaining immature $F_2$ embryos for transformation, controlled sib-pollinations are performed. Immature embryos are isolated at 8-10 days post-pollination when embryos are approximately 1.0 to 2.0 mm in size.

Infection and Co-Cultivation

Maize ears are surface sterilized by scrubbing with liquid soap, immersing in 70% ethanol for 2 minutes, and then immersing in 20% commercial bleach (0.1% sodium hypochlorite) for 30 minutes before being rinsed with sterile water. A suspension *Agrobacterium* cells containing a superbinary vector is prepared by transferring 1-2 loops of bacteria grown on YEP solid medium containing 100 mg/L spectinomycin, 10 mg/L tetracycline, and 250 mg/L streptomycin at 28° C. for 2-3 days into 5 mL of liquid infection medium (LS Basal Medium (Linsmaier and Skoog, 1965), N6 vitamins (Chu et al., 1975), 1.5 mg/L 2,4-Dichlorophenoxyacetic acid (2,4-D), 68.5 gm/L sucrose, 36.0 gm/L glucose, 6 mM L-proline, pH 5.2) containing 100 µM acetosyringone. The solution is vortexed until a uniform suspension is achieved, and the concentration is adjusted to a final density of 200 Klett units, using a Klett-Summerson colorimeter with a purple filter, or an equivalent optical density measured at 600 nm ($OD_{600}$) Immature embryos are isolated directly into a micro centrifuge tube containing 2 mL of the infection medium. The medium is removed and replaced with 1 mL of the *Agrobacterium* solution with a density of 200 Klett units or equivalent $OD_{600}$, and the *Agrobacterium* and embryo solution is incubated for 5 minutes at room temperature and then transferred to co-cultivation medium (LS Basal Medium, N6 vitamins, 1.5 mg/L 2,4-D, 30.0 gm/L sucrose, 6 mM L-proline, 0.85 mg/L $AgNO_3$, 100 µM acetosyringone, 3.0 gm/L Gellan gum (PhytoTechnology Laboratories., Lenexa, Kans.), pH 5.8) for 5 days at 25° C. under dark conditions.

After co-cultivation, the embryos are transferred to selective medium after which transformed isolates are obtained over the course of approximately 8 weeks. For selection of maize tissues transformed with a superbinary plasmid containing a plant expressible pat or bar selectable marker gene, an LS based medium (LS Basal medium, N6 vitamins, 1.5 mg/L 2,4-D, 0.5 gm/L MES (2-(N-morpholino)ethanesulfonic acid monohydrate; PhytoTechnologies Labr.), 30.0 gm/L sucrose, 6 mM L-proline, 1.0 mg/L $AgNO_3$, 250 mg/L cefotaxime, 2.5 gm/L Gellan gum, pH 5.7) is used with Bialaphos (Gold BioTechnology). The embryos are transferred to selection media containing 3 mg/L Bialaphos until embryogenic isolates are obtained. Recovered isolates are bulked up by transferring to fresh selection medium at 2-week intervals for regeneration and further analysis.

Those skilled in the art of maize transformation will understand that other methods of selection of transformed plants are available when other plant expressible selectable marker genes (e.g. herbicide tolerance genes) are used.

Regeneration and Seed Production

For regeneration, the cultures are transferred to "28" induction medium (MS salts and vitamins, 30 gm/L sucrose, 5 mg/L Benzylaminopurine, 0.25 mg/L 2,4-D, 3 mg/L Bialaphos, 250 mg/L cefotaxime, 2.5 gm/L Gellan gum, pH 5.7) for 1 week under low-light conditions ($14~\mu Em^{-2}s^{-1}$) then 1 week under high-light conditions (approximately 89 $\mu Em^{-2}s^{-1}$). Tissues are subsequently transferred to "36" regeneration medium (same as induction medium except lacking plant growth regulators). When plantlets grow to 3-5 cm in length, they are transferred to glass culture tubes containing SHGA medium (Schenk and Hildebrandt (1972) salts and vitamins); PhytoTechnologies Labr.), 1.0 gm/L myo-inositol, 10 gm/L sucrose and 2.0 gm/L Gellan gum, pH 5.8) to allow for further growth and development of the shoot and roots. Plants are transplanted to the same soil mixture as described earlier herein and grown to flowering in the greenhouse. Controlled pollinations for seed production are conducted.

Example 11

Bioassay of Transgenic Maize

Bioactivity of the DIG-303 insecticidal toxins produced in plant cells is demonstrated by conventional bioassay methods (see, for example Huang et al., 2006). One is able to demonstrate efficacy, for example, by feeding various plant tissues or tissue pieces derived from a plant producing a DIG-303 insecticidal toxin to target insects in a controlled feeding environment. Alternatively, protein extracts may be prepared from various plant tissues derived from a plant producing the DIG-303 insecticidal toxin and the extracted proteins incorporated into artificial diet bioassays as previously described herein. It is to be understood that the results of such feeding assays are to be compared to similarly conducted bioassays that employ appropriate control tissues from host plants that do not produce a DIG-303 insecticidal toxin, or to other control samples.

REFERENCES

An, G., Watson, B. D., Stachel, S., Gordon, M. P., Nester, E. W. (1985) New cloning vehicles for transformation of higher plants. EMBO J. 4:277-284.

Altschul, S. F., Gish, W., Miller, W., Myers, E. W., Lipman, D. J. (1990) Basic local alignment search tool. J. Mol. Biol. 215:403-410.

Altschul, S. F., Madden, T. L., Schaffer, A. A., Zhang, J., Zhang, Z., Miller, W., Lipman, D. J. (1997) Gapped BLAST and PSI-BLAST: a new generation of protein database search programs. Nucl. Acids Res. 25:3389-3402.

Armstrong, C. L., Green, C. E., Phillips, R. L. (1991) Development and availability of germplasm with high TypeII culture formation response. Maize Genet. Coop. Newslett. 65:92-93.

Aronson, A. I., Han, E.-S., McGaughey, W., Johnson, D. (1991) The solubility of inclusion proteins from *Bacillus thuringiensis* is dependent upon protoxin composition and is a factor in toxicity to insects. Appl. Environ. Microbiol. 57:981-986.

Aronson, A. I., Geng, C., Wu. L. (1999) Aggregation of *Bacillus thuringiensis* Cry1A toxins upon binding to target insect larval midgut vesicles. Appl. Environ. Microbiol. 65:2503-2507.

Arvidson, H., Dunn, P. E., Strand, S., Aronson, A. I. (1989) Specificity of *Bacillus thuringiensis* for lepidopteran larvae: factors involved in vivo and in the structure of a purified toxin. Molec. Microbiol. 3:1533-1543.

Ausubel et al., eds. (1995) *Current Protocols in Molecular Biology*, Chapter 2 (Greene Publishing and Wiley-Interscience, New York).

Bailey, J. M., Shenov, N. R., Ronk, M., and Shively, J. E., (1992) Automated carboxy-terminal sequence analysis of peptides. Protein Sci. 1:68-80.

Beltz, G. A., Jacobs, K. A., Eickbush, T. H., Cherbas, P. T., Kafatos, F. C. (1983) Isolation of multigene families and determination of homologies by filter hybridization methods. In Wu, R., Grossman, L., Moldave, K. (eds.) Methods of Enzymology, Vol. 100 Academic Press, New York pp. 266-285.

Bown, D. P., Wilkinson, H. S., Jongsma, M. A., Gatehouse, J. A. (2004) Characterization of cysteine proteinases responsible for digestive proteolysis in guts of larval western corn rootworm (*Diabrotica virgifera*) by expression in the yeast *Pichia pastoris*. Insect Biochem. Molec. Biol. 34:305-320.

Bravo, A., Gill, S. S., Soberon, M. (2007) Mode of action of *Bacillus thuringiensis* Cry and Cyt toxins and their potential for insect control. Toxicon 49:423-435.

Caruthers, M. H., Kierzek, R., Tang, J. Y. (1987) Synthesis of oligonucleotides using the phosphoramidite method. Bioactive Molecules (Biophosphates Their Analogues) 3:3-21.

Christeller, J. T., Laing, W. A., Markwick, N. P., Burgess, E. P. J. (1992) Midgut protease activities in 12 phytophagous lepidopteran larvae: dietary and protease inhibitor interactions. Insect Biochem. Molec. Biol. 22:735-746.

Chu, C. C., Wand, C. C., Sun, C. S., Hsu, C., Yin, K. C., Chu, C. Y., Bi, F. Y. (1975) Establishment of an efficient medium for anther culture of rice through comparative experiments on the nitrogen sources. Scientia Sinica 18:659-668.

Crameri, A., Cwirla, S., Stemmer, W. P. C. (1996a) Construction and evolution of antibody-phage libraries by DNA shuffling. Nat. Med. 2:100-103.

Crameri, A., Whitehom, E. A., Tate, E., Stemmer, W. P. C. (1996b) Improved green fluorescent protein by molecular evolution using DNA shuffling. Nat. Biotech. 14:315-319.

Crameri, A., Dawes, G., Rodriguez, E., Silver, S., Stemmer, W. P. C. (1997) Molecular evolution of an arsenate detoxification pathway by DNA shuffling. Nat. Biotech. 15:436-438.

Crickmore N., Zeigler, D. R., Feitelson J., Schnepf, E., Van Rie J., Lereclus D., Baum J., and Dean D. H. (1998) Revision of the Nomenclature for the *Bacillus thuringiensis* Pesticidal Crystal Proteins Microbiol. Mol. Biol. Reviews 62:807-813.

de Maagd, R. A., Kwa, M. S., van der Klei, H., Yamamoto, T., Schipper, B., Vlak, J. M., Stiekema, W. J., Bosch, D. (1996) Domain III substitution in *Bacillus thuringiensis* delta-endotoxin CryIA(b) results in superior toxicity for *Spodoptera exigua* and altered membrane protein recognition. Appl. Environ. Microbiol. 62:1537-1543.

de Maagd, R. A., Bravo, A., Berry, C., Crickmore, N., Schnepf, E. (2003) Structure, diversity, and evolution of protein toxins from spore-forming entomopathogenic bacteria. Annu. Rev. Genet. 37:409-433.

Diaz-Mendoza, M., Farinos, G. P., Castanera, P., Hernandez-Crespo, P., Ortego, F. (2007) Proteolytic processing of native Cry1Ab toxin by midgut extracts and purified trypsins from the Mediterranean corn borer *Sesamia nonagrioide*. J. Insect Physiol. 53:428-435.

Englemann, F., Geraerts, W. P. M., (1980) The proteases and the protease inhibitor in the midgut of *Leucophaea maderae*. J. Insect Physiol. 261:703-710.

Fabrick, J., Oppert, C., Lorenzen, M. D., Morris, K., Oppert, B., Jurat-Fuentes, J. L. (2009) A novel *Tenebrio molitor* cadherin is a functional receptor for *Bacillus thuringiensis* Cry3Aa toxin. J. of Biological Chem. 284(27):18401-18410.

Fraley, R. T., Rogers, S. G., Horsch, R. B. (1986) Genetic transformation in higher plants. Crit. Rev. Plant Sci. 4:1-46.

Gazit, E., La Rocca, P., Sansom, M. S. P., Shai, Y. (1998) The structure and organization within the membrane of the helices composing the pore-forming domain of *Bacillus thuringiensis* delta-endotoxin are consistent with an "umbrella-like" structure of the pore. Proc. Nat. Acad. Sci. USA 95:12289-12294.

Ge, A., Rivers, D., Milne, R., Dean, D. H. (1991) Functional domains of *Bacillus thuringiensis* insecticidal crystal proteins. Refinement of *Heliothis virescens* and *Trichoplusia ni* specificity domains on CryIA(c). J. Biol. Chem. 266:17954-17958.

Gillikin, J. W., Bevilacqua, S., Graham, J. S. (1992) Partial characterization of digestive tract proteinases from western corn rootworm larvae, *Diabrotica virgifera*. Arch. Insect Biochem. Physiol. 19:285-298.

Gomez, I., Sanchez, J., Miranda, R., Bravo, A., Soberon, M. (2002) Cadherin-like receptor binding facilitates proteolytic cleavage of helix alpha-1 in domain I and oligomer pre-pore formation of *Bacillus thuringiensis* Cry1Ab toxin. FEBS Lett. 513:242-246.

Haider, M. Z., Knowles, B. H., Ellar, D. J. (1986) Specificity of *Bacillus thuringiensis* var. *colmeri* insecticidal δ-endotoxin is determined by differential proteolytic processing of the protoxin by larval gut proteases. Eur. J. Biochem. 156:531-540.

Heckel, D. G., Gahan, L. J., Baxter, S. W., Zhao, J-Z., Shelton, A. M., Gould, F., Tabashnik, B. E. (2007) The diversity of *Bt* resistance genes in species of Lepidoptera. J. Invert. Pathol. 95:192-197.

Hepburn, A. G., White, J., Pearson, L., Maunders, M. J., Clarke, L. E., Prescott, A. G. Blundy, K. S. (1985) The use of pNJ5000 as an intermediate vector for the genetic manipulation of *Agrobacterium* Ti-plasmids. J. Gen. Microbiol. 131:2961-2969.

Hoagland, D. R., Anion, D. I. (1950) The water-culture method of growing plants without soil. Calif. Agr. Expt. Sta. Circ. 347.

Hofte, H., de Greve, H., Seurinck, J., Jansens, S., Mahillon, J., Ampe, C., Vandekerckhove, J., Vanderbruggen, H., van Montagu, M., Zabeau, M., Vaeck, M. (1986) Structural and functional analysis of a cloned delta endotoxin of *Bacillus thuringiensis* berliner 1715. Eur. J. Biochem. 161:273-280.

Honée, G., Convents, D., Van Rie, J., Jansens, S., Peferoen, M., Visser, B. (1991) The C-terminal domain of the toxic fragment of a *Bacillus thuringiensis* crystal protein determines receptor binding. Mol. Microbiol. 5:2799-2806

Horton, R. M., Hunt, H. D., Ho, S. N., Pullen, J. K., Pease, L. R. (1989) Engineering hybrid genes without the use of restriction enzymes: gene splicing by overlap extension. Gene 77:61-68.

Huang, F., Rogers, L. B., Rhett, G. H. (2006) Comparative susceptibility of European corn borer, southwestern corn borer, and sugarcane borer (Lepidoptera: Crambidae) to Cry1Ab protein in a commercial *Bacillus thuringiensis* corn hybrid. J. Econ. Entomol. 99:194-202.

Huang, K-X., Badger, M., Haney, K., Evans, S. L. (2007) Large scale production of *Bacillus thuringiensis* PS149B1 insecticidal proteins Cry34Ab1 and Cry35Ab1 from *Pseudomonas fluorescens*. Prot. Express. Purific. 53:325-330.

Janmaat, A. F., Myers, A. H. (2003) Rapid evolution and the cost of resistance to *Bacillus thuringiensis* in greenhouse populations of cabbage loopers, *Trichoplusia ni*. Proc. Royal Soc. London. Ser. B, Biolog. Sci. 270:2263-2270.

Janmaat, A. F., Myers, A. H. (2005) The cost of resistance to *Bacillus thuringiensis* varies with the host plant of *Trichoplusia ni*. Proc. Royal Soc. London. Ser. B, Biolog. Sci. 272:1031-1038.

Karlin, S., Altschul, S. F. (1990) Methods for assessing the statistical significance of molecular sequence features by using general scoring schemes. Proc. Natl. Acad. Sci. USA 87:2264-2268.

Karlin, S., Altschul, S. F. (1993) Applications and statistics for multiple high-scoring segments in molecular sequences. Proc. Natl. Acad. Sci. USA 90:5873-5877.

Keller, G. H., Manak, M. M. (1993) DNA Probes, Background, Applications, Procedures. Stockton Press, New York, N.Y.

Knight, J. S., Broadwell, A. H., Grant, W. N., Shoemaker, C. B. (2004) A Strategy for Shuffling Numerous *Bacillus thuringiensis* Crystal Protein Domains. J. Econ. Entomol. 97:1805-1813.

Koiwa, H., Shade, R. E., Zhu-Salzman, K., D'Urzo, M. P., Murdock, L. L., Bressan, R. A., Hasegawa, P. M. (2000) A plant defensive cystatin (soyacystatin) targets cathepsin L-like digestive cysteine proteinases (DvCALs) in the larval midgut of western corn rootworm *Diabrotica virgifera virgifera*. FEBS Letters 471:67-70.

Larson, S. M., England, J. L., Desjarlais, J. R., Pande, V. S. (2002) Thoroughly sampling sequence space: Large-scale protein design of structural ensembles. Protein Sci. 11:2804-2813.

Lee, L.-Y., Gelvin, S. B. (2008) T-DNA binary vectors and systems. Plant Physiol. 146: 325-332.

Linsmaier, E. M., Skoog, F. (1965) Organic growth factor requirements of tobacco tissue. Physiologia Plantarum 18:100-127.

Littlefield, J. W. (1964) Selection of hybrids from matings of fibroblasts in vitro and their presumed recombinants. Science 145:709-710.

Meinkoth, J., Wahl, G. (1984) Hybridization of nucleic acids immobilized on solid supports. Anal. Biochem. 138:267-284.

Myers, E., Miller, W. (1988) Optimal alignments in linear space. CABIOS 4:11-17.

Naimov, S., Weemen-Hendriks, M., Dukiandjiev, S., de Maagd, R. A. (2001) *Bacillus thuringiensis* delta-endotoxin Cry1 hybrid proteins with increased activity against the Colorado potato beetle. Appl. Environ. Microbiol. 11:5328-5330.

Needleman, S. B., Wunsch, C. D. (1970) A general method applicable to the search for similarities in the amino acid sequence of two proteins. J. Mol. Biol. 48:443-453.

Nunez-Valdez, M.-E., Sanchez, J., Lina, L., Guereca, L., Bravo, A. (2001) Structural and functional studies of alpha-helix 5 region from *Bacillus thuringiensis* Cry1Ab delta-endotoxin. Biochim. Biophys. Acta, Prot. Struc. Molec. Enzymol. 1546:122-131.

Ochoa-Campuzano, C., Real, M. D., Martinez-Ramirez, A. C., Bravo, A., Rausell, C. (2007) An ADAM metalloprotease is a Cry3Aa *Bacillus thuringiensis* toxin receptor. Biochem. Biophys. Res. Commun 362:437-442.

Pigott, C. R., Ellar, D. J. (2007) Role of receptors in *Bacillus thuringiensis* crystal toxin activity. Microbiol. Molec. Biol. Rev. 71:255-281.

Rang, C., Vachon, V., de Maagd, R. A., Villalon, M., Schwartz, J.-L., Bosch, D., Frutos, R., Laprade R. (1999) Interaction between functional domains of *Bacillus thuringiensis* insecticidal crystal proteins. Appl. Environ. Microbiol. 65:2918-2925.

Sambrook, J., Fritsch, E. F., Maniatis, T. (1989) *Molecular Cloning: A Laboratory Manual* (2nd ed., Cold Spring Harbor Laboratory Press, Plainview, N.Y.)

Schenk, R. U., Hildebrandt, A. C. (1972) Medium and techniques for induction and growth of monocotyledonous and dicotyledonous plant cell cultures. Can. J. Bot. 50:199-204

Schnepf, H. E., Tomczak, K., Ortega, J. P., Whiteley, H. R. (1990) Specificity-determining regions of a Lepidopteran-specific insecticidal protein produced by *Bacillus thuringiensis*. J. Biol. Chem. 265:20923-20930.

Soberon, M., Pardo-Lopez, L., Lopez, I., Gomez, I., Tabashnik, B. E., Bravo, A. (2007) Engineering modified *Bt* toxins to counter insect resistance. Science 318:1640-1642.

Squires, C. H., Retallack, D. M., Chew, L. C., Ramseier, T. M., Schneider, J. C., Talbot, H. W. (2004) Heterologous protein production in *P. fluorescens*. Bioprocess Intern. 2:54-59.

Stemmer, W. P. C. (1994a) DNA shuffling by random fragmentation and reassembly: in vitro recombination for molecular evolution. Proc. Natl. Acad. Sci. USA 91:10747-10751

Stemmer, W. P. C. (1994b) Rapid evolution of a protein in vitro by DNA shuffling. Nature 370: 389-391.

Stemmer, W. P. C. (1995) Searching sequence space. Bio/Technology 13:549-553.

Stewart, L. (2007) Gene synthesis for protein production. Encylopedia of Life Sciences. John Wiley and Sons, Ltd.

Stewart, L., Burgin, A. B., (2005) Whole gene synthesis: a gene-o-matic future. Frontiers in Drug Design and Discovery 1:297-341.

Suggs, S. V., Miyake, T., Kawashime, E. H., Johnson, M. J., Itakura, K., R. B. Wallace, R. B. (1981) ICN-UCLA Symposium. Dev. Biol. Using Purified Genes, D. D. Brown (ed.), Academic Press, New York, 23:683-69

Tabashnik, B. E., Finson, N., Groeters, F. R., Moar, W. J., Johnson, M. W., Luo, K., Adang, M. J. (1994) Reversal of resistance to *Bacillus thuringiensis* in *Plutella xylostella*. Proc. Nat. Acad. Sci. USA 91:4120-4124.

Tabashnik, B. E., Gassmann, A. J., Crowder, D. W., Carriere, T. (2008) Insect resistance to *Bt* crops: evidence versus theory. Nat. Biotech. 26:199-202.

Taggart, R. T., Samloff, I. M. (1983) Stable antibody-producing murine hybridomas. Science 219:1228-1230.

Thie, N. M. R., Houseman J. G. (1990) Identification of cathepsin B, D and H in the larval midgut of Colorado potato beetle, *Leptinotarsa decemlineata* say (Coleoptera: Chrysomelidae) Insect Biochem. 20:313-318.

Thompson, J. D., Higgins, D. G., Gibson, T. J. (1994) CLUSTAL W: improving the sensitivity of progressive multiple sequence alignment through sequence weighting, position-specific gap penalties and weight matrix choice. Nucl. Acids Res. 22:4673-4680.

Tijssen, P. (1993) Laboratory Techniques in Biochemistry and Molecular Biology Hybridization with Nucleic Acid Probes, Part I, Chapter 2. P. C. van der Vliet (ed.), (Elsevier, N.Y.)

Varshavsky, A. (1997) The N-end rule pathway of protein degradation. Genes to Cells 2:13-28.

Walters, F. S., Slatin, S. L., Kulesza, C. A., English, L. H. (1993) Ion channel activity of N-terminal fragments from CryIA(c) delta-endotoxin. Biochem. Biophys. Res. Commun. 196:921-926.

Wehrmann, A., Van Vliet, A., Opsomer, C., Botterman, J., Schulz, A. (1996) The similarities of bar and pat gene products make them equally applicable for plant engineers. Nat. Biotechnol. 14:1274-1278.

Weigel, D., Glazebrook, J. (eds.) (2002) *Arabidopsis*: A Laboratory Manual. Cold Spring Harbor Press, Cold Spring Harbor, N.Y., 354 pages.

Wolfson, J. L., Murdock, L. L. (1990) Diversity in digestive proteinase activity among insects. J. Chem. Ecol. 16:1089-1102.

Worley, C. K., Ling, R., Callis, J. (1998) Engineering in vivo instability of firefly luciferase and *Escherichia coli* β-glucuronidase in higher plants using recognition elements from the ubiquitin pathway. Plant Molec. Biol. 37:337-347.

We claim:

1. An isolated, treated, or formulated DIG-303 insecticidal toxin polypeptide comprising an amino acid sequence selected from the group consisting of
   (a) residues 11 to 685 of SEQ ID NO:2, comprising a C-terminal protoxin portion of a Cry toxin other than DIG-303; and
   (b) residues 11 to 685 of SEQ ID NO:2 with up to 20 amino acid substitutions, deletions, or modifications that do not adversely affect expression or activity of the toxin encoded by SEQ ID NO:2.

2. The isolated, treated, or formulated polypeptide of claim 1 comprising an amino acid sequence of SEQ ID NO:2.

3. The isolated, treated, or formulated polypeptide of claim 1, wherein the C-terminal protoxin portion comprises the C-terminal protoxin portion of Cry1Ab.

4. A method for controlling a pest population comprising contacting said population with a pesticidally effective amount of the polypeptide of claim 1.

5. The polypeptide of claim 1 having activity against a coleopteran pest or Diamondback moth.

6. The polypeptide of claim 1 having activity against Colorado potato beetle or Diamondback moth.

7. A composition comprising the polypeptide of claim 1.

8. The composition of claim 7, wherein the composition is a sprayable protein composition, encapsulated protein composition, or bait matrix that comprises the formulated DIG-303 insecticidal toxin.

9. A nucleic acid construct comprising a heterologous nucleic acid sequence that is recombinantly linked to a sequence encoding the polypeptide of claim 1.

10. The nucleic acid construct of claim 9, wherein the heterologous nucleic acid sequence is a promoter sequence capable of driving expression in a plant.

11. The nucleic acid construct of claim 9, wherein the sequence encoding the polypeptide is codon-optimized for expression in a plant.

12. The nucleic acid construct of claim 10, wherein the promoter is capable of driving expression in corn and the sequence encoding the polypeptide is codon optimized for expression in corn.

13. The nucleic acid construct of claim 9, wherein the sequence encoding the polypeptide comprises SEQ ID NO:1 or SEQ ID NO:3.

14. The nucleic acid construct of claim 12, wherein the construct is a vector and the vector comprises SEQ ID NO:3.

15. The nucleic acid construct of claim 10, wherein the promoter is capable of driving expression in potato and the sequence encoding the polypeptide is codon optimized for expression in potato.

16. A transgenic plant comprising the nucleic acid construct of claim 10 stably incorporated into its genome.

17. A method for protecting a plant from a pest comprising introducing into said plant the construct of claim 9.

* * * * *